United States Patent
Moore et al.

(10) Patent No.: US 10,098,746 B1
(45) Date of Patent: Oct. 16, 2018

(54) MEDICAL IMPLANTS HAVING DESIRED SURFACE FEATURES AND METHODS OF MANUFACTURING

(71) Applicant: Nextstep Arthropedix, LLC, Akron, OH (US)

(72) Inventors: Cowan H. Moore, Uniontown, OH (US); Randall R. Theken, Barberton, OH (US); Christopher Lee Fries, Fresno, CA (US); Eric Montgomery Lucas, Stow, OH (US); Richard Barros, Cuyahoga Falls, OH (US)

(73) Assignee: Nextstep Arthropedix, LLC, Akron, OH (US)

( * ) Notice: Subject to any disclaimer, the term of this patent is extended or adjusted under 35 U.S.C. 154(b) by 37 days.

(21) Appl. No.: 15/043,081

(22) Filed: Feb. 12, 2016

Related U.S. Application Data

(60) Provisional application No. 62/116,211, filed on Feb. 13, 2015.

(51) Int. Cl.
*A61F 2/32* (2006.01)
*A61F 2/36* (2006.01)

(52) U.S. Cl.
CPC ............ *A61F 2/3609* (2013.01); *A61F 2/36* (2013.01); *A61F 2250/006* (2013.01)

(58) Field of Classification Search
CPC ...... A61F 2/34; A61F 2/30767; A61F 2/3662; A61F 2002/30914; A61F 2002/30845;
(Continued)

(56) References Cited

U.S. PATENT DOCUMENTS 3,685,058 A    8/1972   Tronzo
4,542,539 A    9/1985   Rowe et al.
(Continued)

FOREIGN PATENT DOCUMENTS

WO    WO2014/172495    10/2014
WO    WO2016/018160    2/2016
WO    WO2016/061148    4/2016

OTHER PUBLICATIONS

Davison, Dale; Acetabular Cup with non-periodic Coating Jun. 18, 2014.
(Continued)

*Primary Examiner* — Brian Dukert
(74) *Attorney, Agent, or Firm* — Middleton Reutlinger

(57) ABSTRACT

In embodiments of the invention, an implant that anchors into bone may have a bone-facing region that comprises a plurality of interconnected struts. The interconnected struts may define local features such as engagement ridges, fins, crests, a macroscopic surface-interrupting feature, a divertor structure, and sawteeth in any combination. Such features may help resist translation or rotation of the implant, and may be conducive to bone ingrowth. Parameters such as local empty volume fraction and local average strut length can be varied, even within the features, by the design of the network of struts. Struts may be tapered. Cantilever struts may also be provided, which may point in a desired direction. The pattern of struts may be specified to the level of dimensions and location of individual struts. The implant may be manufactured by additive manufacturing methods. The mesh of struts may be generated by an algorithm using Voronoi tessellation.

11 Claims, 30 Drawing Sheets

(58) Field of Classification Search
CPC .... A61F 2002/30841; A61F 2002/3412; A61F 2002/3092
See application file for complete search history.

(56) References Cited

U.S. PATENT DOCUMENTS

| | | | |
|---|---|---|---|
| 4,743,262 | A | 5/1988 | Tronzo |
| 5,358,532 | A | 10/1994 | Evans et al. |
| 5,433,750 | A | 7/1995 | Gradinger et al. |
| 5,489,306 | A | 2/1996 | Gorski |
| 5,786,562 | A | 7/1998 | Larson |
| 5,972,032 | A | 10/1999 | Lopez et al. |
| 6,149,689 | A | 11/2000 | Grundei |
| 6,206,924 | B1 | 3/2001 | Timm |
| 6,709,462 | B2 | 3/2004 | Hanssen |
| 6,772,026 | B2 | 8/2004 | Bradbury et al. |
| 6,931,812 | B1 | 8/2005 | Lipscomb |
| 7,018,418 | B2 | 3/2006 | Amrich et al. |
| 7,208,222 | B2 | 4/2007 | Rolfe et al. |
| 7,435,232 | B2 | 10/2008 | Liebschner |
| 7,537,664 | B2 | 5/2009 | O'Neill et al. |
| 7,578,851 | B2 | 8/2009 | Dong et al. |
| 7,597,715 | B2 | 10/2009 | Brown et al. |
| 7,632,575 | B2 | 12/2009 | Justin et al. |
| 7,713,454 | B2 | 5/2010 | Larsson |
| 7,815,847 | B2 | 10/2010 | Gennaro et al. |
| 7,931,462 | B2 | 4/2011 | Mattes |
| 8,066,770 | B2 | 11/2011 | Rivard et al. |
| 8,066,778 | B2 | 11/2011 | Meridew et al. |
| 8,070,821 | B2 | 12/2011 | Roger |
| 8,268,099 | B2 | 9/2012 | O'Neill et al. |
| 8,268,100 | B2 | 9/2012 | O'Neill et al. |
| 8,350,186 | B2 | 1/2013 | Jones et al. |
| 8,430,930 | B2 | 4/2013 | Hunt |
| 8,454,705 | B2 | 6/2013 | Pressacco et al. |
| 8,475,503 | B2 | 7/2013 | Denoziere et al. |
| 8,556,981 | B2 | 10/2013 | Jones et al. |
| 8,700,198 | B2 | 4/2014 | Conway et al. |
| 8,702,806 | B2 | 4/2014 | Balay et al. |
| 8,715,366 | B2 | 5/2014 | Borden |
| 8,728,164 | B2 | 5/2014 | Buck et al. |
| 8,728,387 | B2 | 5/2014 | Jones et al. |
| 8,795,381 | B2 | 8/2014 | Podolsky |
| 8,814,567 | B2 | 8/2014 | Zhang et al. |
| 8,828,311 | B2 | 9/2014 | Medina et al. |
| 8,864,826 | B2 | 10/2014 | Pressacco |
| 8,888,862 | B2 | 11/2014 | McDonnell et al. |
| 8,992,703 | B2 | 3/2015 | O'Neill et al. |
| 8,992,825 | B2 | 3/2015 | Li et al. |
| 9,034,048 | B2 | 5/2015 | Choren |
| 9,039,741 | B2 | 5/2015 | Lambrecht et al. |
| 9,073,265 | B2 | 7/2015 | Snis |
| 9,079,248 | B2 | 7/2015 | Ackelid |
| 9,125,756 | B2 | 9/2015 | Ullrich, Jr. et al. |
| 9,126,167 | B2 | 9/2015 | Ljungblad |
| 9,132,510 | B2 | 9/2015 | Nashner et al. |
| 9,135,374 | B2 | 9/2015 | Jones et al. |
| 9,149,345 | B2 | 10/2015 | Lomicka et al. |
| 9,180,010 | B2 | 11/2015 | Dong et al. |
| 9,237,950 | B2 | 1/2016 | Hensley et al. |
| 9,364,896 | B2 | 6/2016 | Christensen et al. |
| 9,415,137 | B2 | 8/2016 | Meridew et al. |
| 9,445,909 | B2 | 9/2016 | Cohen et al. |
| 9,456,901 | B2 | 10/2016 | Jones et al. |
| 9,549,823 | B2 | 1/2017 | Hunt et al. |
| 9,572,669 | B2 | 1/2017 | Hunt et al. |
| 2006/0254200 | A1 | 11/2006 | Clarke et al. |
| 2008/0249598 | A1 | 10/2008 | Sherry |
| 2008/0288083 | A1 | 11/2008 | Axelsson et al. |
| 2009/0326671 | A1 | 12/2009 | Schofield |
| 2010/0070022 | A1 | 3/2010 | Kuehling |
| 2010/0298950 | A1* | 11/2010 | McDonnell ......... A61F 2/30771 623/23.53 |
| 2011/0008754 | A1 | 1/2011 | Bassett et al. |
| 2011/0014081 | A1 | 1/2011 | Jones et al. |
| 2011/0022180 | A1 | 1/2011 | Melkent et al. |
| 2011/0196495 | A1 | 8/2011 | Hunt |
| 2011/0313532 | A1* | 12/2011 | Hunt ................... A61F 2/30767 623/18.11 |
| 2012/0215310 | A1 | 8/2012 | Sharp et al. |
| 2012/0251980 | A1 | 10/2012 | Bassett et al. |
| 2012/0321878 | A1 | 12/2012 | Landon et al. |
| 2013/0030529 | A1 | 1/2013 | Hunt |
| 2013/0123935 | A1 | 5/2013 | Hunt et al. |
| 2013/0158672 | A1 | 6/2013 | Hunt |
| 2013/0199748 | A1 | 8/2013 | Christensen et al. |
| 2013/0218282 | A1 | 8/2013 | Hunt |
| 2013/0264749 | A1 | 10/2013 | Jones et al. |
| 2013/0268085 | A1 | 10/2013 | Dong et al. |
| 2013/0325129 | A1 | 12/2013 | Huang |
| 2014/0010951 | A1 | 1/2014 | Vargas et al. |
| 2014/0025181 | A1 | 1/2014 | Vanasse et al. |
| 2014/0107786 | A1 | 4/2014 | Geisler et al. |
| 2014/0121776 | A1 | 5/2014 | Hunt |
| 2014/0257507 | A1 | 9/2014 | Wang et al. |
| 2014/0277548 | A1 | 9/2014 | Cohen et al. |
| 2014/0288649 | A1 | 9/2014 | Hunt |
| 2014/0288650 | A1 | 9/2014 | Hunt |
| 2014/0371863 | A1 | 12/2014 | Vanasse et al. |
| 2015/0012109 | A1 | 1/2015 | Moreau et al. |
| 2015/0018956 | A1 | 1/2015 | Steinmann et al. |
| 2015/0045903 | A1 | 2/2015 | Neal |
| 2015/0134063 | A1 | 5/2015 | Steinmann et al. |
| 2015/0150681 | A1 | 6/2015 | Ricci et al. |
| 2015/0216668 | A1 | 8/2015 | Smith |
| 2015/0282945 | A1 | 10/2015 | Hunt |
| 2015/0282946 | A1 | 10/2015 | Hunt |
| 2016/0038289 | A1 | 2/2016 | Noble |
| 2016/0157908 | A1 | 6/2016 | Cawley et al. |
| 2016/0287388 | A1 | 10/2016 | Hunt et al. |
| 2016/0287405 | A1 | 10/2016 | Hunt et al. |
| 2017/0056178 | A1 | 3/2017 | Sharp et al. |

OTHER PUBLICATIONS

Depuy Orthopaedics, Inc.; Pinnacle Acetabular Cup System—Design Rationale Jan. 1, 2002.
Smith & Nephew; R3 Acetabular System—Design Rationale Jan. 1, 2008.
Within Technologies Ltd; Within Medical Brochure Jan. 17, 2014.
Medacta International; MPACT Technical Sheet.
Within Technologies Ltd; Within Medical Basic Guide Jan. 17, 2014.
Within Technologies Ltd; Within Medical Technical Manual May 14, 2014.
Wright Medical Technology, Inc.; BioFoam Cancellous Titanium Matrix Fixation with Bite. Jan. 1, 2009.
Zimmer, Inc.; Zimmer Continuum Acetabular System Jan. 1, 2010.
Renovis Surgical Technologies, Inc.; Tesera Trabecular Technology (T3) Porous Structure Jan. 1, 2014.

* cited by examiner

550

500

500
700

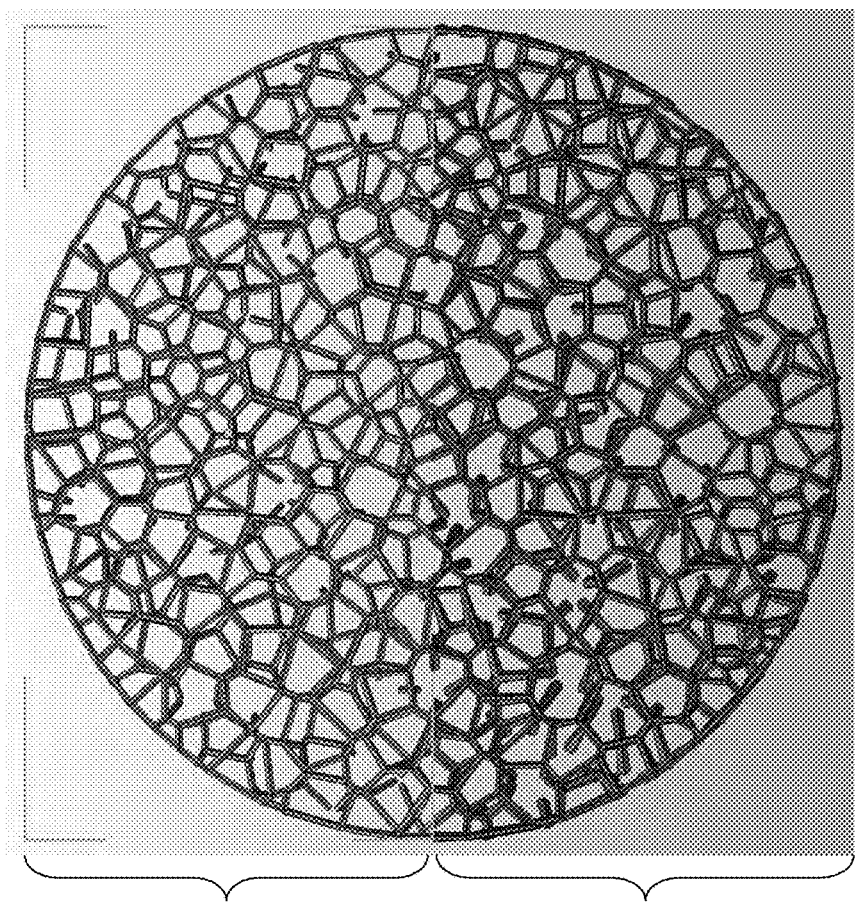
Struts of uniform cross-section — Fig. 8B — Some struts are tapered
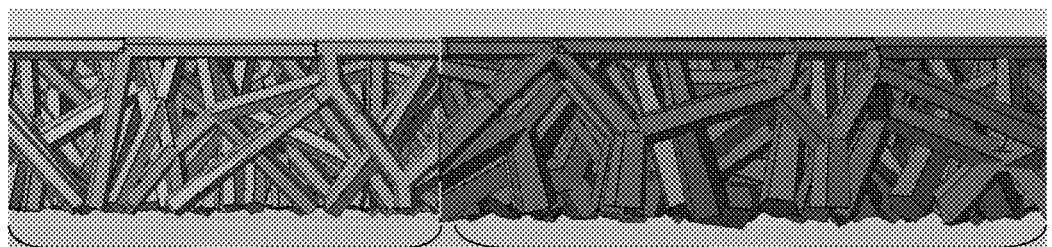
Struts of uniform cross-section — Fig. 8C — Some struts are tapered Fi. 10A

MEDICAL IMPLANTS HAVING DESIRED SURFACE FEATURES AND METHODS OF MANUFACTURING

CROSS-REFERENCE TO PRIOR APPLICATION

This application claims priority to and benefit under 35 U.S.C. § 119(e) to currently U.S. Provisional Application Ser. No. 62/116,211, filed on Feb. 13, 2015, which is incorporated herein by reference.

FIELD OF THE INVENTION

Embodiments of the invention pertain to medical implants that interface with bone.

BACKGROUND OF THE INVENTION

Implants that interface with natural bone need to form a strong mechanical bond with the natural bone, both at the time of implantation and after bone growth onto or into the implant has occurred. Various geometries and manufacturing techniques for implants are known. Some implants have used rough or porous surfaces or coatings that are conducive to ingrowth or ongrowth of bone. However, it is still desirable to improve the design and manufacture of implants, and to encourage bone growth and formation of a strong mechanical bond between the implant and the bone.

SUMMARY OF THE INVENTION

In an embodiment of the invention, there may be provided an implantable device, comprising a first region that is substantially solid; and a second region, adjacent to the first region, the second region comprising a plurality of interconnected struts, some of the struts joining the first region, the struts having an average strut length, the struts defining openings between the struts through which bone can grow, wherein the second region comprises struts that are connected at both of their ends to other struts and are outermost struts and define an exterior having a bone-facing enveloping surface, and wherein the bone-facing enveloping surface has at least one concavity and at least one convexity.

In an embodiment of the invention, there may be provided an implantable device, comprising a first region that is substantially solid; and a second region, adjacent to the first region, the second region comprising a plurality of interconnected struts, some of the struts joining the first region, the struts having an average strut length, the struts defining openings between the struts through which bone can grow, wherein the second region comprises struts that are connected at both of their ends to other struts and are outermost struts and define an exterior having a bone-facing enveloping surface, and wherein the second region has a variation of local empty volume fraction within the second region, or the second region has a variation of local average strut length within the second region, or both.

In an embodiment of the invention, there may be provided an implantable device, comprising a first region that is substantially solid; and a second region, adjacent to the first region, the second region comprising a plurality of interconnected struts, some of the struts joining the first region, the struts having an average strut length, the struts defining openings between the struts through which bone can grow, wherein the second region comprises struts that are connected at both of their ends to other struts and are outermost struts and define an exterior having a bone-facing enveloping surface, and wherein at least some of the struts are tapered along their length.

In an embodiment of the invention, there may be provided an implantable device, comprising a first region that is substantially solid; and a second region, adjacent to the first region, the second region comprising a plurality of interconnected struts, some of the struts joining the first region, the struts having an average strut length, the struts defining openings between the struts through which bone can grow, wherein the second region comprises struts that are connected at both of their ends to other struts and are outermost struts and define an exterior having a bone-facing enveloping surface, wherein the second region further comprises a plurality of cantilevers that extend outward from vertices at or near the local enveloping surface and extend beyond the bone-facing enveloping surface, and wherein each of the cantilevers has a respective lengthwise cantilever direction, and at each of the cantilevers there is a respective local normal vector that is normal to the local enveloping surface of the implantable device at a location of the cantilever, and the cantilever direction points more towards a rear of the implantable device than does the local normal vector.

In an embodiment of the invention, there may be provided an implantable device, comprising a first region that is substantially solid; and a second region, adjacent to the first region, the second region comprising a plurality of interconnected struts, some of the struts joining the first region, the struts having an average strut length, the struts defining openings between the struts through which bone can grow, wherein the second region comprises struts that are connected at both of their ends to other struts and are outermost struts and define an exterior having a bone-facing enveloping surface, and wherein the implantable device further comprises a plurality of cantilevers that extend outward from the first region.

In an embodiment of the invention, there may be provided an implantable device, comprising a first region that is substantially solid; and a second region, adjacent to the first region, the second region comprising a plurality of interconnected struts, some of the struts joining the first region, the struts having an average strut length, the struts defining openings between the struts through which bone can grow, wherein the second region comprises struts that are connected at both of their ends to other struts and are outermost struts and define an exterior having a bone-facing enveloping surface, and wherein the implantable device further comprises a plurality of loop structures, the loop structures being curved or segmented and connecting at both of their ends to vertices, the loop structures extending beyond the bone-facing enveloping surface.

In an embodiment of the invention, there may be provided an implant comprising a first region that is substantially solid; and a second region, adjacent to the first region, the second region comprising a plurality of interconnected struts, some of the struts joining the first region, the struts having an average strut length, the struts defining openings between the struts through which bone can grow, wherein the second region comprises struts that are connected at both of their ends to other struts and are outermost struts and define an exterior enveloping surface, wherein the exterior enveloping surface has a smooth region that is generally smooth on a size scale greater than the average strut length, and wherein the exterior enveloping surface also has, extending outward from the smooth region, at least one sharp feature that is sharp on a size scale of the average strut length or smaller, wherein the sharp feature and the smooth region are both made of some of the plurality of the struts.

In an embodiment of the invention, there may be provided an implant comprising a first region that is substantially solid; and a second region, adjacent to the first region, the second region comprising a plurality of interconnected struts, some of the struts joining the first region, the struts having an average strut length, the struts defining openings between the struts through which bone can grow, wherein the second region comprises struts that are connected at both of their ends to other struts and are outermost struts and define an exterior having a bone-facing enveloping surface, wherein the bone-facing enveloping surface has at least one concavity and at least one convexity.

In an embodiment of the invention, there may be provided an implant comprising a first region that is substantially solid; a second region, adjacent to the first region, the second region comprising a plurality of interconnected struts, some of the struts joining the first region, the struts having an average strut length, the struts defining openings between the struts through which bone can grow; and the second region having a second region external enveloping shape at a size scale larger than an average strut length, wherein the implant has a longitudinal axis and, in a cross-section taken perpendicular to the longitudinal axis, has a perimeter, wherein at some places the perimeter is farther from the longitudinal axis than the perimeter is at other places, by at least one of the average strut length.

In an embodiment of the invention, there may be provided an implant comprising a first region that is substantially solid; a second region, adjacent to the first region, the second region comprising a plurality of interconnected struts, some of the struts joining the first region, the struts having an average strut length, the struts defining openings between the struts through which bone can grow; and wherein the second region comprises struts that are connected at both of their ends to other struts and are outermost struts and define an exterior enveloping surface, wherein at least some of the struts connect at respective ends to others of the struts at vertices, wherein the second region external shape has a majority external enveloping surface occupying a majority of an exterior of the second region, wherein the second region external shape further comprises a macroscopic surface-interrupting feature that differs from the majority external enveloping surface, wherein the macroscopic surface-interrupting feature comprises some of the interconnected struts.

In an embodiment of the invention, there may be provided an implant comprising a first region that is substantially solid; and a second region, adjacent to the first region, the second region being rough-surfaced or porous or comprising a plurality of interconnected struts, wherein on an exterior thereof, the implant comprises a fin that has a fin long direction, and wherein, on the exterior, the implant further comprises a divertor structure, wherein the divertor structure is located rearward from the fin along a direction of advancement the implant, wherein the divertor structure is not in line with the fin along the fin long direction.

In an embodiment of the invention, there may be provided an implant comprising a first region that is substantially solid; and a second region, adjacent to the first region, the second region comprising a plurality of interconnected struts, some of the struts joining the first region, the struts having an average strut length, the struts defining openings between the struts through which bone can grow, wherein external-most struts that connect at both ends to other struts define, at a size scale larger than the average strut length, a local enveloping surface, wherein the second region further comprises a plurality of cantilevers that extend outward from vertices at the local enveloping surface, wherein each of the cantilevers has a respective lengthwise cantilever direction, and at each of the cantilevers there is a respective local normal vector that is normal to the local enveloping surface of the implant, and the cantilever direction points more towards a rear of the implant than does the local normal vector.

In an embodiment of the invention, there may be provided an implant comprising a first region that is substantially solid; and a second region, adjacent to the first region, the second region comprising a plurality of interconnected struts, some of the struts joining the first region, the struts having an average strut length, the struts defining openings between the struts through which bone can grow, wherein external-most struts that connect at both ends to other struts define, at a size scale larger than the average strut length, a local envelope surface, further comprising a plurality of cantilevers that extend outward from vertices at the enveloping surface, wherein the implant has an external shape that is at least approximately a hemisphere having an equator and a pole, and the cantilevers exist at or near the equator of the implant but a region closer to the pole of the implant is free of the cantilevers.

In an embodiment of the invention, there may be provided an implant comprising a first region that is substantially solid; and a second region, integrally joined to the first region, the second region comprising a plurality of interconnected struts in a predetermined geometry that fully defines a location of each of the struts, the struts being at least approximately straight, wherein at least some of the struts connect to others of the struts at vertices, wherein the predetermined geometry of the plurality of the struts is non-repeating.

In embodiments of the invention, an implant having a first region that may be a non-bone-facing region and a second region that may be a bone-facing region may be designed containing thousands of struts in the second region such that the design specifies the location, placement, and dimensions of each strut. The implant may be manufactured to correspond to the design, within manufacturing tolerances, and multiple implants may be manufactured that are substantially identical to each other, within manufacturing tolerances. The manufacturing may be done by additive manufacturing, which may be from powder as a starting material. Joining of powder particles to other powder particles or to already-manufactured parts of the implant may be done by laser or by electron beam or by other means. It is described in embodiments of the invention that the detailed design of the pattern of the struts may be somewhat random and non-repeating. The struts may form a network into or onto which bone can grow. Struts may connect to other struts at vertices. Features that are designed into the pattern of struts (such as engagement ridges, fins, sawteeth, crests etc.) may be made of interconnected struts that smoothly interconnect with the strut pattern of the second region in general. Thus the second region, formed by interconnected struts, may have an overall shape and also have specific local features all defined by a network of interconnected struts. The interconnected-strut region (second region) and the first region, which is more solid, may be made in a single manufacturing process, and in fact with a layer-by-layer manufacturing process, manufacturing such as fusing performed in a given layer may be devoted in one portion of the layer to making solid or nearly-solid material corresponding to a first region, while in another portion of the same layer, the manufacturing such as fusing may be devoted to making portions of struts.

BRIEF DESCRIPTION OF THE ILLUSTRATIONS

Embodiments of the invention are further described in the following illustrations.

FIG. 5B shows, for the second region 200, individual struts both at the exterior and within the region.

FIG. 8B shows the same situation as FIG. 8A, in the form a top view.

FIG. 8C shows the same situation as FIG. 8A, in the form a side view.

FIG. 10A is a similar external view, but three-dimensional and sectioned, showing cantilevers. In this illustration, the solid interior region is present.

DETAILED DESCRIPTION

Figure 1:
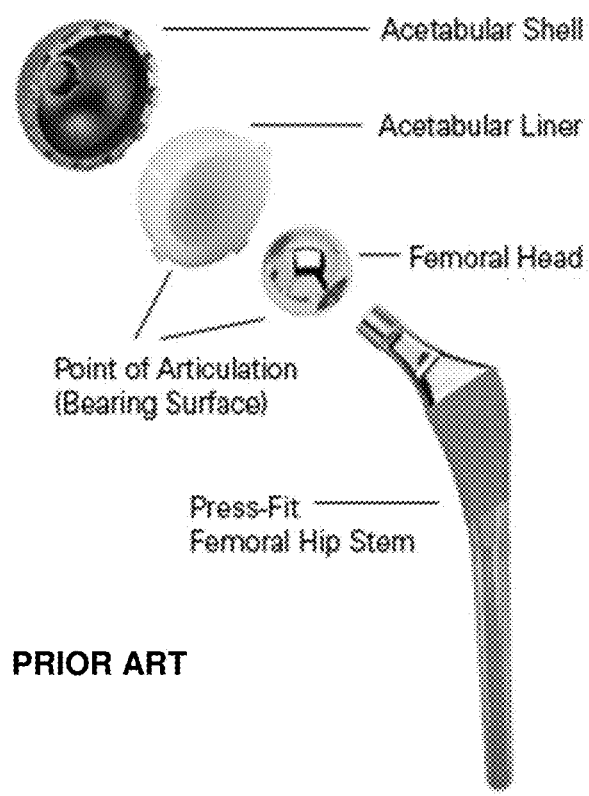
FIG. 1 is a perspective view of a generic hip implant, including an acetabular cup.

Referring now to FIG. 1, there is illustrated a conventional joint replacement prosthesis, which in this illustrated example is for a hip joint replacement prosthesis. Such a prosthesis may comprise a ball element or ball assembly and a cup element or cup assembly that can receive the ball element or ball assembly. As illustrated, the ball assembly may be an assembly in which a ball and a stem are manufactured individually and are then assembled to each other. Alternatively, the ball and the stem may be manufactured integral with each other. Each of the two elements or assemblies may be shaped suitably to anchor to respective bone. As illustrated, one element or assembly is suitable to anchor into a long bone having a central canal, and this element or assembly has an elongated stem. As illustrated, another element or assembly is shaped to anchor into a relatively massive piece of bone, and this element or assembly has an external shape that is somewhat convex without being significantly elongated. As illustrated, the prosthesis comprises one each of an element or assembly whose bone-engaging shape is elongated and an element or assembly whose bone-engaging shape is non-elongated. However, it is also possible that a joint prosthesis in general could have both elements/assemblies being elongated, or, both elements/assemblies being non-elongated. As illustrated, the elongated bone-engaging shape is associated with the ball assembly, and the non-elongated bone-engaging shape is associated with the cup assembly. However, other variations are also possible. Typically, at least some of these components may comprise a metal such as titanium or a titanium alloy, but other materials are also possible.

For a hip prosthesis, typically the cup element or assembly may be implanted in the acetabulum of the pelvis, and the ball element or assembly may be implanted into the canal of the femur. Replacement joint prostheses are also possible for various other joints of the body, and may have similar parts such as cups and stems, but the orientations of the ball and the cup may vary, and the geometry of interaction with bone on respective sides of the joint may vary such as being elongated or not elongated as appropriate. In known prostheses, the external, bone-facing surface of an implant may also comprise, on a small size scale such on the order of 1 mm or less, an irregular pattern that is conducive to ingrowth or ongrowth of bone. Examples of such irregular pattern include a coating, or a sintered geometry, or other type of surface or texturing. The material of the bone-facing surface or coating or texturing may be either the same as the material of other parts of the implant, or a different material.

A cup element may be used in conjunction with a liner that is received inside the cup and that may have its own internal concave shape that receives the ball. Such a liner may be made of a polymeric material, or alternatively a ceramic material or other material.

Regions and Struts

Figure 2A:
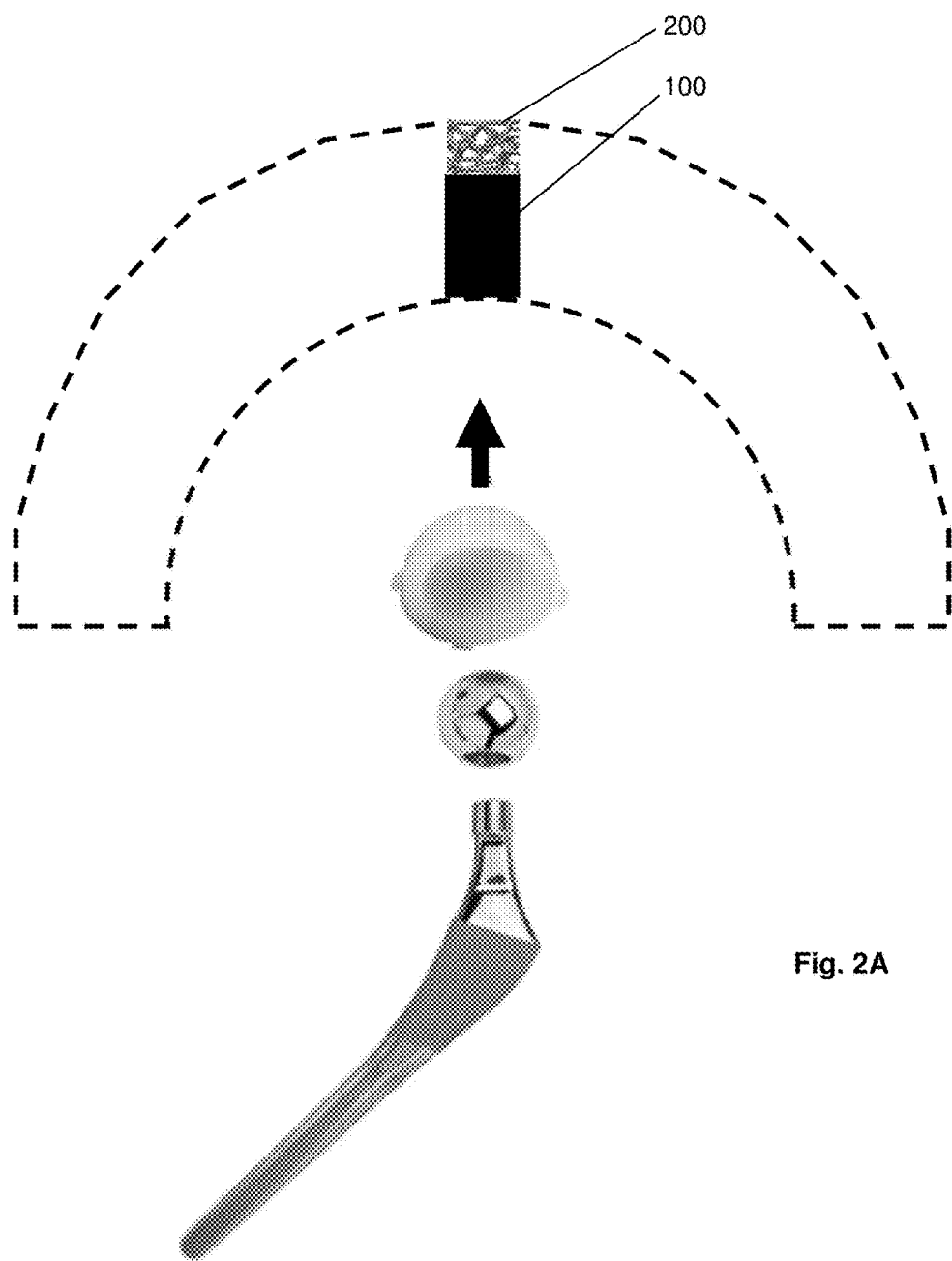
FIG. 2A illustrates placement of the features of an embodiment of the invention, on an acetabular cup or shell of a hip prosthesis.
Figure 2B:
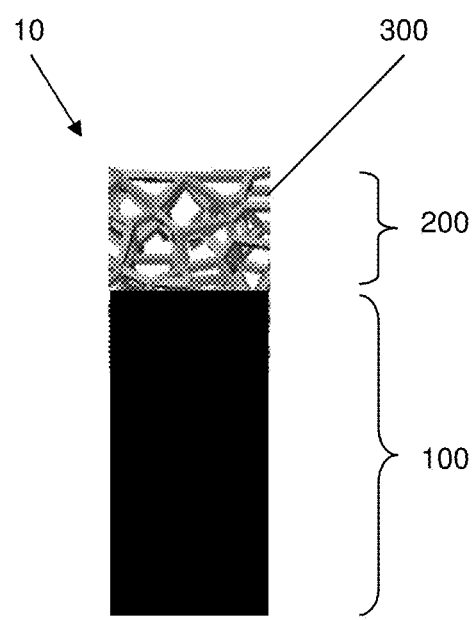
FIG. 2B is an enlargement of a portion of FIG. 2A, illustrating both a first region that is fully dense and a second region that comprises a plurality of struts.
Figure 2C:
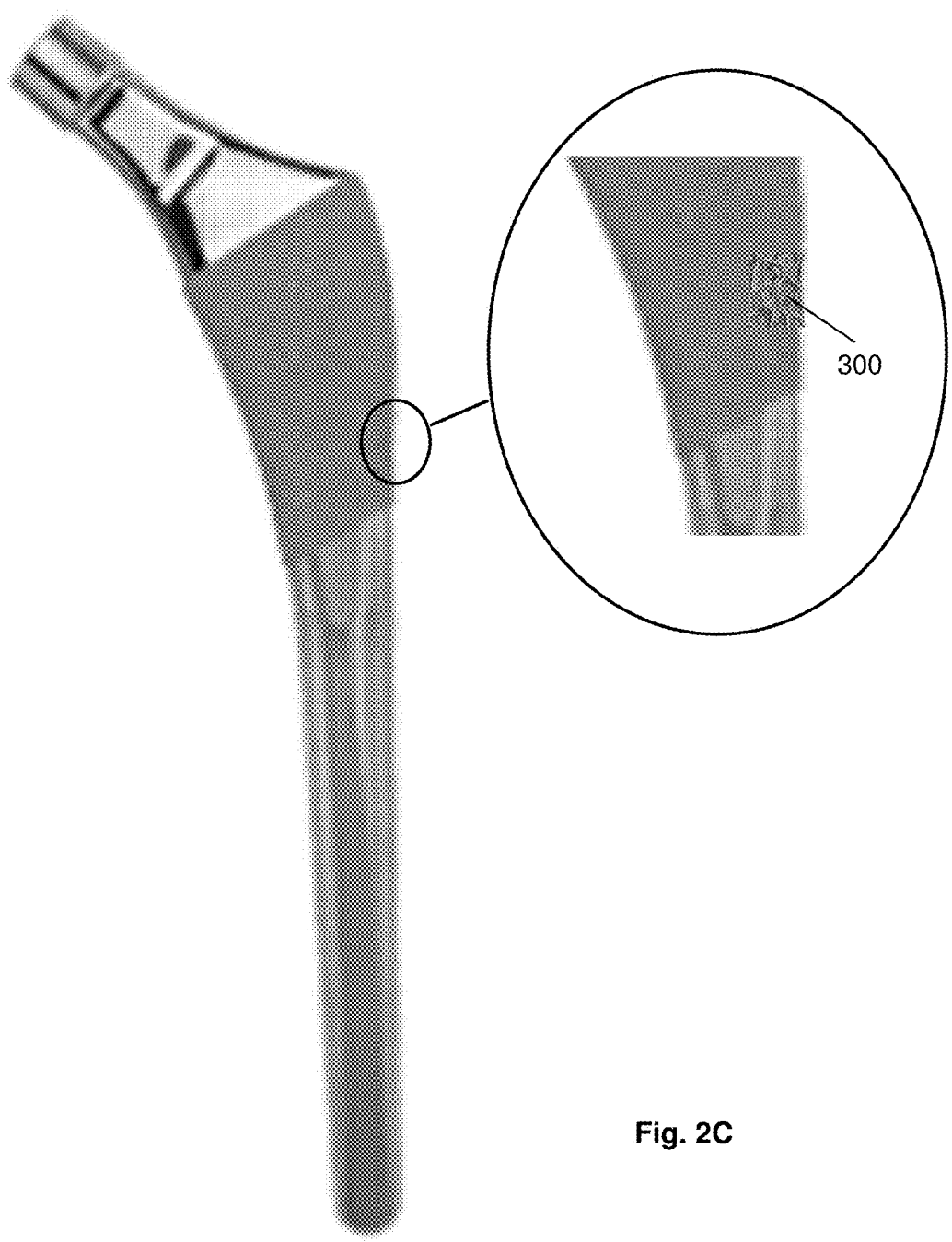
FIG. 2C is similar to FIG. 2B but illustrating placement of the features on a femoral stem component of a hip prosthesis.

Referring now to FIGS. 2A-2C, it is illustrated that in an embodiment of the invention, there may be provided an implant 10 that includes a first region 100 and a second region 200. As illustrated, the second region 200 may be a bone-facing region. The first region 100 may be a region that is somewhat removed from bone. For example, a cup type implant might have a convex exterior, and the second region 200 may face bone, and the first region 100 may be substantially solid metal, which may itself have a cup-shaped interior. As another example, a stem type implant may have second region 200 that faces bone, and first region 100 may be the interior of the stem. More generally, at least some of the first region 100 may face away from bone.

The first region 100 may be fully dense, meaning that it is entirely solid material. In a similar sense, it is possible that the first region 100 might not be perfectly fully dense, and yet may be close enough to fully dense so that it functions similarly to fully dense material, such as in terms of structural strength. For example, depending on the manufacturing process, it is possible that the first region 100 might contain occasional small inclusions or voids containing a gas such as air, or even vacuum. The first region 100 may contain a modest number of internal voids that do not connect to the interface between the first region 100 and the second region 200, or alternatively or in addition it could even have a small number of voids that do connect to the interface between the first region 100 and the second region 200. As an example, the first region 100 could have a local density that is greater than 90% of the solid density that the same material would have in a completely solid condition.

The implant 10 may further comprise a second region 200 that comprises a plurality of struts 300. The second region 200 may be on the external or bone-facing side of the implant 10, relative to the first region 100. The second region 200 may be structurally connected to the first region 100. The second region 200 may comprise an array of interconnected struts 300. Some of the struts 300 may be connected to the first region 100. The second region 200 may further include within itself empty space between the struts 300, that is, space that is not occupied by any of the struts 300.

A strut 300 may generally be a component that has an identifiable direction of greatest dimension and is structurally connected to at least one other strut 300 or to first region 100. Strut 300 may have two identifiable end points. Struts 300 may be straight but need not be exactly straight. A strut 300 may have along its length a region of somewhat constant cross-section, but this is not essential. A strut 300 may also have an enlarged region that can be thought of as a meniscus near an end of a strut 300 or where the strut 300 connects to another strut 300 or to first region 100. A strut 300 may have a centerline that defines a path of points that are centroids of cross-sections of the strut 300, with the centerline going generally along the identifiable direction of greatest length of the strut 300. It can be noted that the depiction of a strut 300 shown in FIG. 2 may be an idealization of a shape of actual struts, and the same comment applies to other Figures as well. Some of the struts 300 may be connected to the first region 100, while other struts 300 may be connected to still other struts 300 without being connected to the first region 100. The second region 200 may have at its external surface a mesh of struts 300 at its surface defining an identifiable external or imaginary enveloping surface. Struts 300 that define the enveloping surface may be struts that connect at both of their ends to other struts.

In connection with the description of cross-sectional properties of struts, it is further possible that a strut may have a taper from one of its ends to its other end such that the cross-sectional area of the strut is larger toward one end of the strut than it is toward the other end of the strut. For example, the end of the strut having the larger cross-sectional area may be joined to or may be closer to the solid or substantially solid first region 100. Such a tapering feature may provide a gradual transition of strength, a less abrupt transition than would be the case for untapered struts. If struts are tapered as described, not all struts have to be so tapered. In terms of cross-sectional shape, struts may be approximately cylindrical (round cross-section), or triangular prismatic (triangular cross-section), or of rectangular cross-section, or generally any desired cross-sectional shape.

An array of struts 300 may define, between the struts 300, open spaces in which bone can grow, such that eventually bone can grow to surround the struts 300 and embed the struts 300 in bone. A "vertex" is defined to be the intersection point where two or more struts 300 meet, specifically where the centerlines of the respective struts 300 intersect with each other.

In embodiments of the invention, the locations of the struts 300 may be predetermined and defined to such a degree of detail and exactness that the same pattern of struts 300 could be manufactured repeatedly any number of times, resulting in any number of manufactured items that are substantially identical to each other even at the level of detail of the number of struts and the location, orientation, interconnection pattern and dimensions of every strut 300.

As is further discussed elsewhere herein, the implant 10 can be thought of as an integral manufactured piece some of which is solid and some of which is a region that contains a certain amount of empty space between and among struts 300. As discussed elsewhere herein, struts 300 may have a variety of lengths within a given implant.

As a non-limiting example, the second region 200 can have a thickness of several lengths of typical struts 300. A typical or average strut length may be in the range of from tens of microns to hundreds of microns or thousands of microns. An implant 10 may comprise thousands of struts 300, or tens of thousands or more of struts 300. Empty space between struts 300 may, for example be defined by struts 300 that may have an average dimension in the hundreds of microns. For example, a characteristic dimension of a cell (space enclosed by struts that are near each other) may be in the range of 400 microns to 750 microns. The thickness of region 200, measured from the external enveloping surface to the interface between first region 100 and second region 200, may be approximately 1 millimeter. The number of cells in that thickness may, on average, be more than one, for example several cells.

Observable in FIGS. 2A-2D is a portion of the external surface that, on a size scale greater than the dimensions of the struts 300, has an external enveloping shape that is either flat or curved in a simple curvature that corresponds to an overall external shape of the implant 10. Such an external shape may occupy at least a portion of the external or bone-facing surface of the implant 10.

Enveloping Shapes that are Axisymmetric

In general, an axisymmetric surface is a surface that could be formed by revolution of a generatrix curve or shape around an axis of revolution. Shapes that are axisymmetric include spheres, hemispheres, spheroids, ellipsoids, cylinders, cones and frusta of cones. For those shapes, the genetratrix is either a curve or a line. Other shapes of generatrix that are more complicated can also be used to produce other surfaces of revolution, which are still axisymmetric. In contrast, examples of shapes that are not axisymmetric include those just-mentioned shapes if they contain additional features that occur only at certain angles with respect to the axis of revolution and do not occur at other angular locations with respect to the axis of revolution.

Figure 3A:
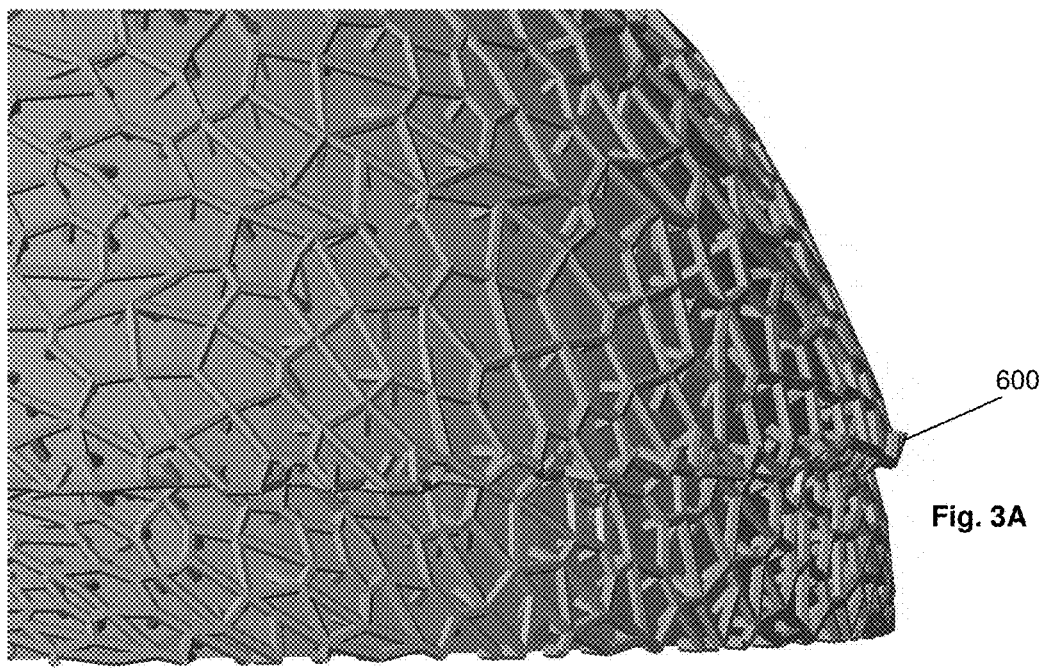
FIG. 3A is an external view of a shape such as a generally hemispherical shape having a feature that may be referred to as an engagement ridge, which extends in a circumferential direction around the circumference of the implant.
Figure 3B:
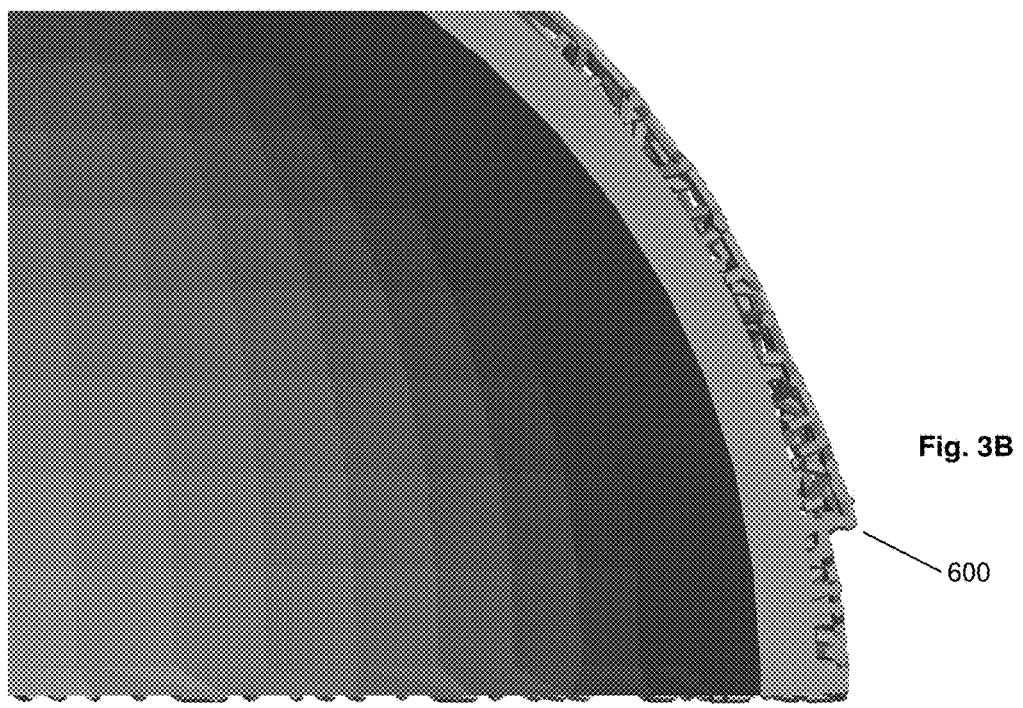
FIG. 3B is a cross-section of FIG. 3A.

Referring now to FIGS. 3A-3B, in an embodiment of the invention, there could be provided an implant 10 that has an external surface that has an engagement ridge 600 going around the entire circumference of the second region 200, which is on the external or bone-facing surface of the implant 10. The engagement ridge 600, in cross-section, can resemble a tooth having a local sharpness. For such a surface, the generatrix would be a curve that includes the tooth or sharpness feature that is visible in cross-section. If the exterior of the implant 10 is at least approximately hemispherical, this engagement ridge 600 may be oriented like a line of latitude on a spherical globe. The direction of the tooth or its local sharpness may point toward the rear of the implant 10, with respect to the direction of motion for implantation of the implant 10 into a surgical site. In the illustrated case of a hemispherical implant 10, the direction of the local engagement ridge 600 may point toward the equator of the hemisphere. The engagement ridge 600 and its orientation may be such that the implant 10 can pass into a bone site more easily than it can move in the reverse direction exiting the bone site. The engagement ridge 600 or engagement ridges 600 could have a particular placement or distribution on the surface of an at-least-approximately-hemispherical implant. With continued analogy to a globe, if the hemisphere is thought of as having an equator and a pole, the engagement ridge(s) 600 may exist primarily near the equator or closer to the equator, and not so much or not at all in the polar region of implant 10.

The engagement ridge 600 may be made fully or at least partially of struts 300. The struts that make up the engagement ridge 600 and second region 200, i.e., both the engagement ridge 600, and the generally hemispherical shape of the remainder of second region 200 that does not have an engagement ridge 600, may all be part of a continuous interconnected network of struts 300.

In FIGS. 3A-3B, the engagement ridge 600 is shown as extending entirely around the full angular circumference of implant 10, but in a more general situation, a structure resembling engagement ridge 600 might be placed such that it occupies less than the full angular circumference of implant 10. This latter would be an example of an implant design that is not axisymmetric.

Enveloping Shapes that are Non-Axisymmetric

Referring now to FIGS. 4A-7E, there are shown embodiments of the invention that are not completely axisymmetric.

Figure 4A:
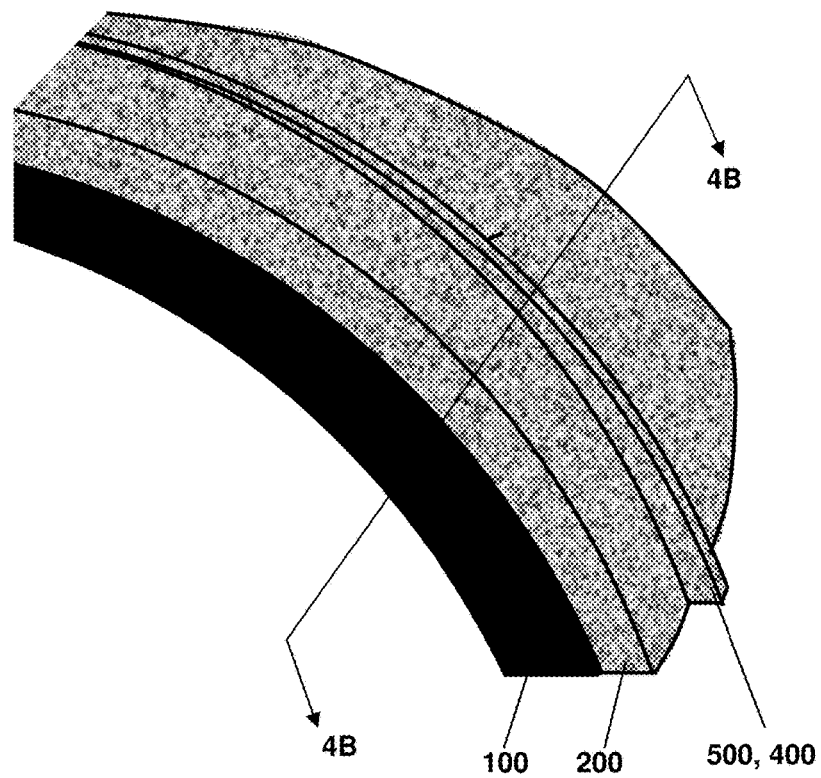
FIG. 4A is a three-dimensional view of a hemispherical implant that has extending therefrom a fin of somewhat rectangular cross-sectional shape.
Figure 4B:
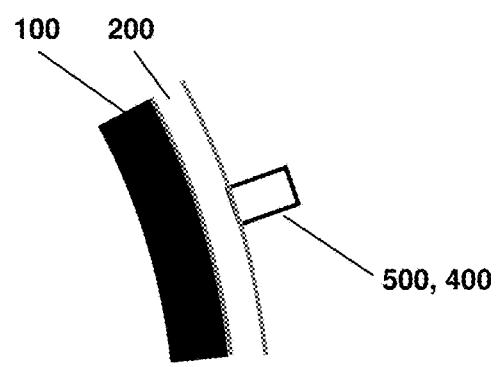
FIG. 4B is a sectional view of FIG. 4A.

An example is the macroscopic surface-interrupting feature, such as fins 500, which is illustrated in FIGS. 4A and 4B. FIG. 4B is a sectional view of FIG. 4A. The fins 500, as illustrated in FIGS. 4A and 4B, may be somewhat step-wise or abrupt in their shape relative to the overall surface of the implant 10. The fins 500 shown in FIGS. 4A-4B are sufficiently well-defined so that their enveloping shape may exhibit side surfaces and possibly other surfaces that may be at least approximately flat. The fins 500 may be made of an array of interconnected struts 300, which may be continuous and interconnected with, or substantially continuous and interconnected with, the array of interconnected struts 300 elsewhere in second region 200 of implant 10. For simplicity of illustration in FIGS. 4A-4B, the struts are not shown. The fins of FIGS. 4A-4B have a cross-sectional shape that is generally rectangular.

Figures 4C, 4D:
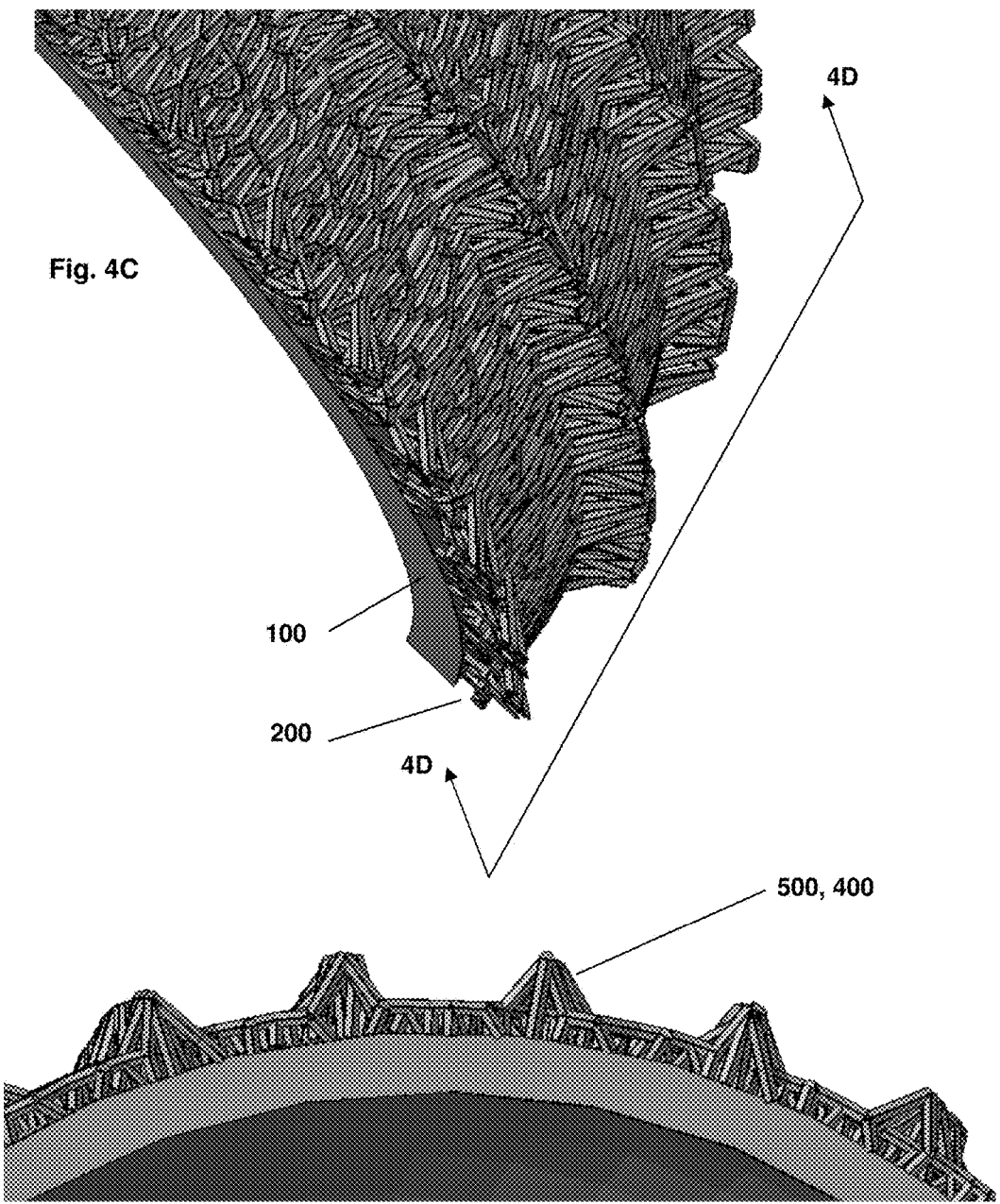
FIG. 4C is a three-dimensional view of a hemispherical implant that has extending therefrom a fin of somewhat triangular cross-sectional shape.
FIG. 4D is a bottom view of FIG. 4C

FIGS. 4C-4D also show fins 500, but these fins 500 have a cross-sectional shape that is generally triangular. FIG. 4D is a bottom view of FIG. 4C. The fins 500 are shown as being made of an array of interconnected struts 300, which may be continuous and interconnected with, or substantially continuous and interconnected with, the array of interconnected struts 300 elsewhere in second region 200 of implant 10.

Figure 5A:
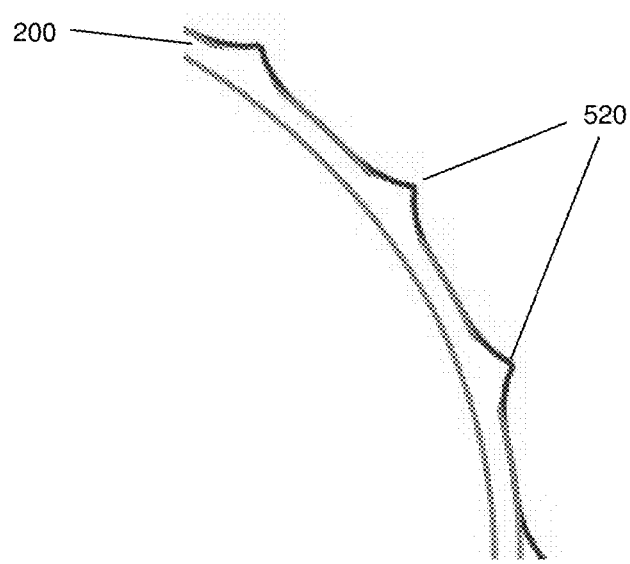
FIG. 5A is an outline of a second region for a shape such as a generally hemispherical shape having a macroscopic surface-interrupting feature that is a somewhat gradual shape, added onto a majority external surface shape. For clarity of illustration, in FIG. 5A, individual struts are not shown.
Figure 5B:
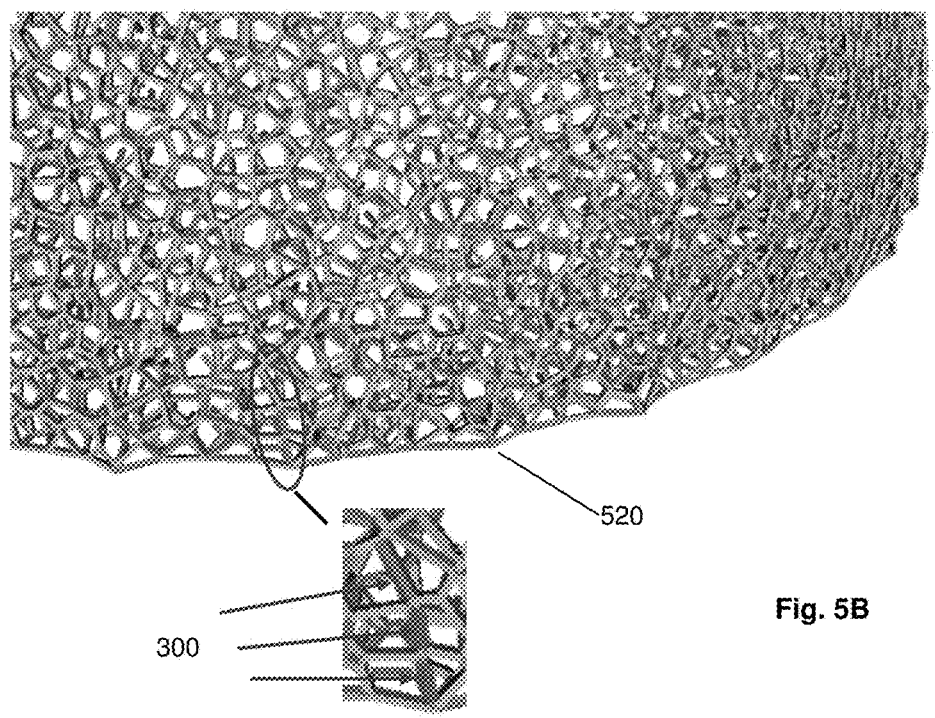
FIG. 5B is an external view of a shape as described in FIG. 5A.

Referring now to FIGS. 5A and 5B, for an embodiment of the invention, there are shown views of a generally hemispherical exterior surface that also has some localized features, which have similarities to the fins of FIGS. 4A-4D but are less dramatic or abrupt in their overall enveloping shape. Both the generally hemispherical exterior surface and the localized features are made of a plurality of interconnected struts. FIG. 5A is an outline of a second region 200 (first region 100 not shown) for a shape such as a generally hemispherical shape that has some additional features. For clarity of illustration, individual struts are not shown in FIG. 5A. This outline illustrates both a majority external surface shape (generally hemispherical) and a macroscopic surface-interrupting feature 400, which may be described as resembling crests 520, which may be superimposed onto the majority external surface shape. As illustrated, in cross-section in FIG. 5A, the majority external surface shape in cross-section is circular, and the macroscopic surface-interrupting feature 400 is crests 520 or peaks that extend beyond the circular shape. FIG. 5B shows a possible actual strut construction of the second region 200 in which there is illustrated both a majority external surface shape that is a portion of a hemisphere, and macroscopic surface-interrupting features that are crests 520 or peaks, with all of these features being made of an array of interconnected struts 300. It can be considered that what is shown in FIGS. 5A-5B are features that are less abrupt or prominent than the fins 500 of FIGS. 4A-4D. For clarity of illustration in FIG. 5B, individual struts are shown but the underlying solid first region 100 is not shown.

As illustrated in FIGS. 5A and 5B, the externally-facing surface of implant 10 may comprise a majority external surface shape that occupies a majority of the envelope of the external surface of second region 200. It is possible that the majority external surface shape may be axisymmetric and, specifically in this situation, hemispherical. FIG. 5A is a view of an outline shape, which could be seen by looking at the end of implant 10 that shows the interior of the hemisphere, and for clarity of illustration, individual struts are not shown. FIG. 5B is an external view, for a shape such as a generally hemispherical shape with some additional features. FIG. 5B is a view of the second region 200 showing individual struts both at the exterior and within the region. FIG. 5B can be seen by looking at the end of implant 10 that is exterior convex. For clarity of illustration, first region 100, which would be solid, is not shown in FIG. 5B, nor is it shown in FIG. 5A.

It is illustrated in FIGS. 5A-5B that the externally-facing surface of implant 10 may comprise at least one macroscopic surface-interrupting feature 400 that differs from the majority external envelope shape or that interrupts some symmetry of the majority external surface shape. Non-limiting examples of such macroscopic surface-interrupting features, which are further described elsewhere herein, include a fin 500, a crest 520, sawteeth 550, an engagement ridge 600, and a divertor structure 700. Except for an engagement ridge 600, these macroscopic surface-interrupting features 400 may interrupt the overall axisymmetry of the external surface of implant 10.

An engagement ridge 600, a fin 500, a crest 520, a macroscopic surface-interrupting feature 400, or any other feature described herein, may serve purposes such as helping to maintain the position of the implant 10 in bone and resisting motion or change of position of the implant 10 relative to the bone. Non-limiting examples of motion that can be resisted by such macroscopic surface-interrupting features 400 include rotation of the implant 10 around its axis of symmetry, or generally around any axis, after it has been implanted, and translational backing out of the implant 10 along the direction of implantation of the implant 10.

The macroscopic surface-interrupting feature 400 may comprise a plurality of interconnected struts 300. If there are a plurality of macroscopic surface-interrupting features 400, some of them or all of them may comprise a plurality of interconnected struts 300. It is possible that the entirety of a macroscopic surface-interrupting feature 400 may be made of interconnected struts 300, or only a portion of macroscopic surface-interrupting feature 400 may be made of interconnected struts 300. The array of interconnected struts 300 that make up the macroscopic surface-interrupting feature 400 may be substantially continuous with the array of interconnected struts that make up the majority external envelope shape of second region 200. It is discussed elsewhere herein that, alternatively, macroscopic surface-interrupting features 400 could be solid or substantially solid, even if this means interrupting the array of interconnected struts 300.

In FIGS. 5A and 5B, the macroscopic surface-interrupting feature 400 has an external contour that is somewhat sharp at its externally projecting peak, while the rest of the fin or feature is more gradually and gently curved.

Figure 5C:
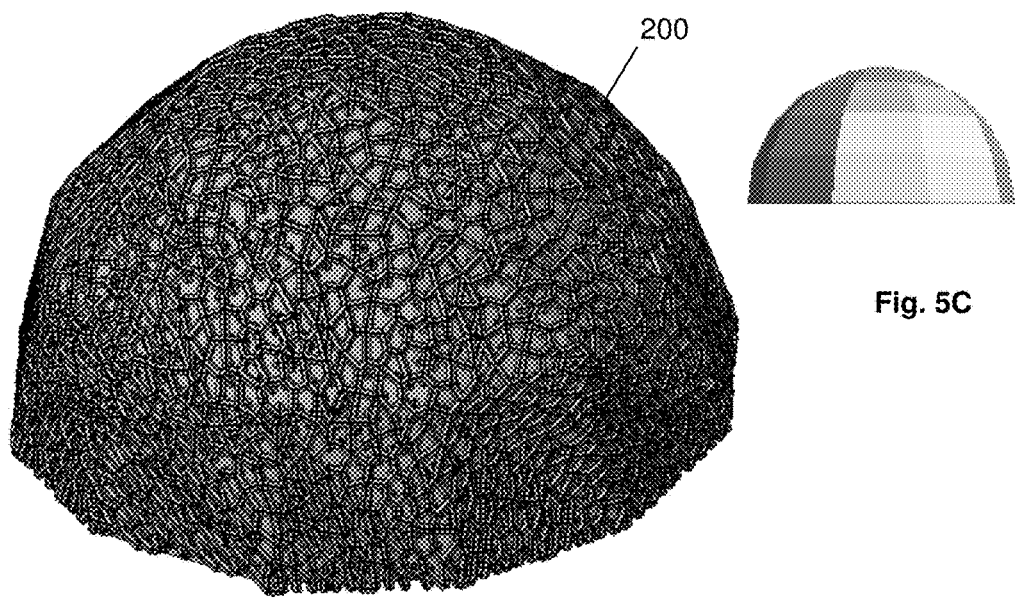
FIG. 5C shows a surface that is generally hemispherical but the envelope of the struts on its exterior has flat facets.
Figure 5D:
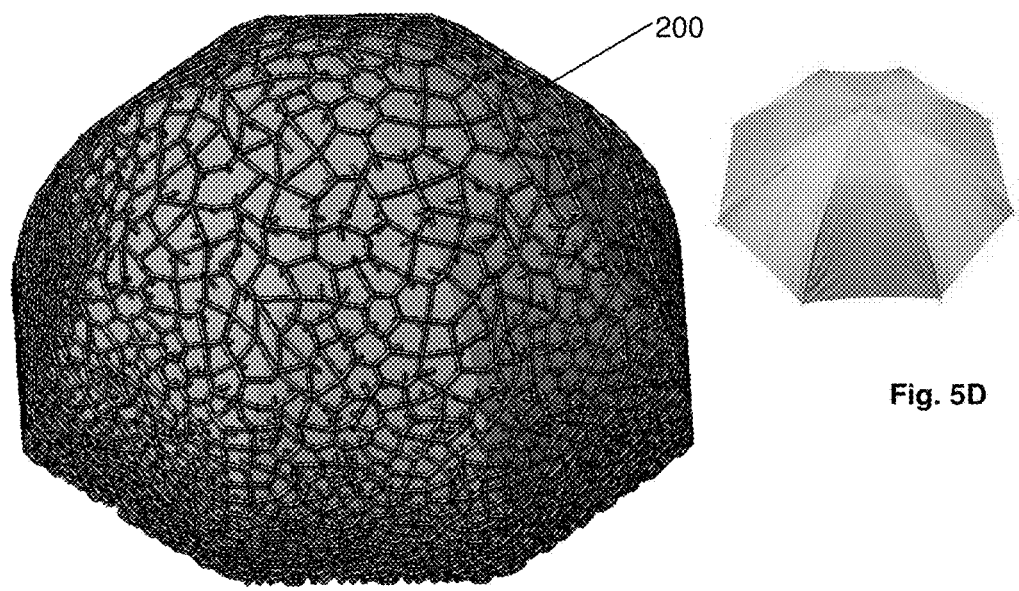
FIG. 5D shows a surface that is generally hemispherical but the envelope of the struts on its exterior has segments that are curved approximately cylindrically.

It is possible that at a feature that is sharp, such as the tip of engagement ridge 600 or a corner of a fin 500 as shown in FIGS. 4A-4B, or a tip of a fin 500 as shown in FIG. 5B, or a tip of a crest 520 as shown in FIG. 5D, the tip of the feature could be a series of struts 300 in succession that are at least approximately parallel to each other or in line with each other, thereby forming a sort of a cutting edge. For example, in FIG. 5B there is highlighted a place where three consecutive struts are at a ridge or peak of a crest or a fin, approximately in line with each other, forming sort of a cutting edge. However, this is not essential.

Yet another possibility is that the external surface of implant 10 might have features that are pertinent to anchoring or might be non-axisymmetric, and yet might not be separable into an identifiably distinct majority external surface shape and an identifiably distinct macroscopic surface-interrupting feature. For example, around a circumference of the implant 10, with the circumference being taken in a section plane that is generally perpendicular to a direction of insertion of the implant 10, the circumference may comprise a sequence of smoothly or continuously varying peaks and valleys. It might happen that the general appearance of the exterior resembles a hemisphere and yet there could be surface portions that do not exactly coincide with a hemispherical shape. For example, the enveloping shape other than at peaks could have, in cross-section, flat panels or segments (as illustrated in FIG. 5C) rather than bidirectionally curved segments that would be characteristic of a perfectly hemispherical surface. The peaks might or might not be identifiably distinct macroscopic surface-interrupting features, as previously described herein, with respect to the surface that contains the valleys, i.e, it might or might not be possible to identify a distinct point or boundary where the majority external surface shape ceases and the macroscopic surface-interrupting feature begins, and yet still the surface might be non-axisymmetric in a mathematical sense. FIG. 5D illustrates yet another such possibility, in which the external shape is composed entirely of curved segments (the individual segments are curved in one direction of curvature, rather than bidirectionally curved as in a traditional hemisphere). All such possibilities are still considered to be embodiments of the invention. It is even possible that both concavities and convexities could be gently curved. In such instance, a cross-section of a generally hemispherical implant 10, taken perpendicular to its axis of symmetry, might resemble a circle with a small sinusoidal variation superimposed on the circle.

The peaks or non-axisymmetric features such as are illustrated in FIGS. 4A-5D may be equiangularly spaced around the circumference of the implant 10, although they do not have to be so spaced. With respect to a center of the cross-section of the implant 10, the difference in radial position between a peak and a valley may be at least one typical or average length of struts 300. All of the features, or at least some of the features, may be made up of struts 300.

Concavities and Convexities

Complex surface shapes, or various of the features referred to herein, may be described in a general way by describing that the external enveloping surface of implant 10 may have both local concavities and local convexities. Again, the external enveloping surface of local concavities and local convexities may be made of arrays of interconnected struts 300. Such arrays of interconnected struts 300 may be continuous and interconnected with, or substantially continuous and interconnected with, the array of interconnected struts 300 elsewhere in second region 200 of implant 10. A concavity may refer, loosely, to a depression in the overall external enveloping surface of the second region 200. A convexity may refer, loosely, to a bump or outward protrusion in the overall external enveloping surface of the second region 200.

For sake of explanation, the presence of both local concavities and local convexities may be in contrast, for example, to a simple perfect hemisphere, which may be convex everywhere (bidirectionally convex) in its bone-facing surface. Similarly, the presence of both local concavities and local convexities would be in contrast in contrast to a simple cylinder or frustoconical surface, which may be convex everywhere in its surface such as its surface that would face the internal canal surface of a medullary canal of a bone. The generally hemispherical exterior shape is, of course, characteristic of the exterior of an acetabular cup or similar implant, while a generally cylindrical or frustoconical exterior surface would be characteristic of a stem such as a femoral stem. The presence of both concavities and convexities in such a surface may help in anchoring the implant 10 to bone, and the presence of both concavities and convexities could make the external surface of the implant 10 sufficiently asymmetric to resist certain kinds of possible motion of the implant 10 with respect to the bone, such as rotation.

Concavities and convexities could be smoothly varying having a fairly large radius of curvature, or they could be fairly sharp, having a small radius of curvature. (In the limiting case, a sharp corner would have a radius of curvature of zero). Concavities and convexities could further be a combination of gentle and sharp radii of curvature, such as having a radius of curvature in one direction that might be gentle and a radius of curvature in another direction that might be sharp. For example, some of the features of the enveloping surface as shown in FIG. 5A-5B are smoothly varying. FIGS. 5A and 5B show gentle radii of curvature on the concavities but a fairly sharp radius of curvature on the convexity. It would also be possible, alternatively, for the convexities to have a relatively gentle radius of curvature. Corners, such as right-angle corners, which are sharp, can be either a convex corner or a concave corner. The fin 500 shown in FIGS. 4A and 4B has some external corners that are fairly sharp and these can be described as convexities also. The same fin 500 has some internal corners that are fairly sharp, and these can be described as concavities also. Any of these concavities and convexities can be made of arrays of interconnected struts as described elsewhere herein, just as the rest of second region 200 can be made of an array of interconnected struts 300. Non-limiting examples of convexities include an engagement ridge, a fin, a fin with teeth, a crest, a peak, and a divertor structure, as discussed elsewhere herein.

Fins

The fin 500 may extend outward relative to a remainder of the majority external surface shape, such as a convex surface, of the implant 10. A fin 500 could be distinct enough that it has identifiable sides, which may be at least approximately flat, or parts of it may be more gentle as might be described by the term crest. Fin 500 may be a shape that comprises multiple struts 300. A fin 500 may have a dimension extending outward, in comparison to the majority external surface shape, that is at least one typical length of a strut 300.

A specific possible shape of implant 10 is a shape in which the exterior of the implant 10 may have a mostly hemispherical shape and, in such a situation, the shape may be described, by analogy with Earth's geography, as having an equator, a pole, and lines of latitude and longitude. In such a situation, the fin 500 may have a path that corresponds to a line of longitude on the hemisphere. More generally, if at least some features of the external surface of implant 10 are axisymmetric around an axis of revolution, the fin 500 may lie generally in a plane that contains the axis of revolution. However, other shapes and paths of fin 500 are possible also (for example, helical or twisting).

If there is a plurality of fins 500 or similar features, the fins 500 or pattern of peaks and valleys can be periodic at equiangular intervals around the equator. However, such equiangular spacing is not essential. The fin(s) 500 may provide an anti-rotation feature that prevents the implant 10, when implanted into bone, from rotating, with respect to the bone, around the axis of revolution of its majority external surface shape. Fins 500 or similar features may be distributed in a repeating pattern and may be substantially identical to each other, which may enable the implant 10 to be repositioned at another position that is different in its angular position around the axis of revolution, if desired. For example, there may be approximately 20 such fins 500 distributed equiangularly around the circumference or equator of the implant 10. There could be 40 such fins 500 or features spaced around the circumference, or some other number. Alternatively, if desired, the angular distribution of the fins 500 around the circumference could be other than equiangular.

The fin 500, at its base joining the majority external surface shape, may have a width, in an equatorial direction, that is at least one strut 300 wide. At its most outward places, the fin 500 may simply comprise only a single strut 300 that extends along the long direction of the fin 500. This may provide a sharpness, to the extent that a feature made of distributed struts 300 can be thought of as having sharpness, which can help the fin 500 to cut into bone. Alternatively, the fin 500 could have multiple strut-lengths even at its tip. The fin 500 may have a height or a dimension extending outward from a remainder of the external or convex surface of the implant 10, such that this dimension tapers or varies in a desired manner. For example, if the implant 10 is at least approximately hemispherical having an equator and a pole, this dimension may be greater in a portion of the implant 10 such as close to the equator, and may taper to a smaller dimension at a portion of the implant 10 such as near the pole. This is illustrated in FIG. 4A, in which the fin height may gradually taper or the fin 500 may gradually disappear upon approaching the pole. Other tapers and configurations of fin 500 are also possible if desired.

A leading edge may refer to a portion of a fin 500 or macroscopic surface-interrupting feature 400 that first encounters bone as the implant 10 is advanced into an intended position in bone. A trailing edge may refer to an edge that is opposed to a leading edge, along a general direction of travel. It is possible that fin 500 could have a leading edge that is sharp. It is possible that the fin 500 could have a trailing edge that is blunt, such as if the fin 500 will be within the region of natural bone when the implant 10 is in its implanted position, such as if the fin 500 does not extend all the way to the equator of an implant 10 that is hemispherical or nearly hemispherical on its exterior surface.

The fin 500 could be made of an array of interconnected struts 300, or at least some of the fin 500 could comprise an array of interconnected struts 300.

As yet another possibility, an external enveloping surface could be made of a plurality of flat segments or a plurality of one-directionally curved segments such as cylindrical segments. These are illustrated in FIGS. 5C and 5D. In FIGS. 5C and 5D, there is illustrated an implant 10 having both a first region 100 and a second region 200, and alongside is illustrated what the implant might look like in the absence of the second region 200. FIG. 5D resembles a conventional umbrella in which it can be appreciated that although the overall shape may approximate a hemisphere, in more detail the surface is defined in curved panels that are curved in one direction only, thereby being like segments of individual cylinders. An enveloping surface as illustrated in either FIG. 5C or FIG. 5D could be the enveloping surface of the array of interconnected struts that makes up second region 200, just as described for other shapes such as engagement ridges and fins. A cylindrical segment (as in FIG. 5D) would have curvature in one direction, but only in one direction. A flat segment or panel (as in FIG. 5C) would have no curvature in any direction. The shapes illustrated in both FIGS. 5C and 5D would have an ability to anchor into bone, such as a prepared hemispherical socket in bone, in a way that prevents or deters or resists rotation of the implant around its longitudinal axis or around the direction of implantation. This may happen in somewhat the same way as would be accomplished by fins, although with a less dramatically-varying shape. Both of these shapes (FIGS. 5C and 5D) could be implanted in a surgical site in which a surgical preparation tool forms a generally hemispherical socket in bone.

It is possible that the adjacent solid region (first region 100) could have generally the same shape as the described enveloping shape. Alternatively, the adjacent first region 100 could have a different shape, such as for example a simple hemisphere. The shape that has just been described in reference to macroscopic surface-interrupting features is the external enveloping shape that envelopes the array of interconnecting struts 300.

Teeth

Figure 6A:
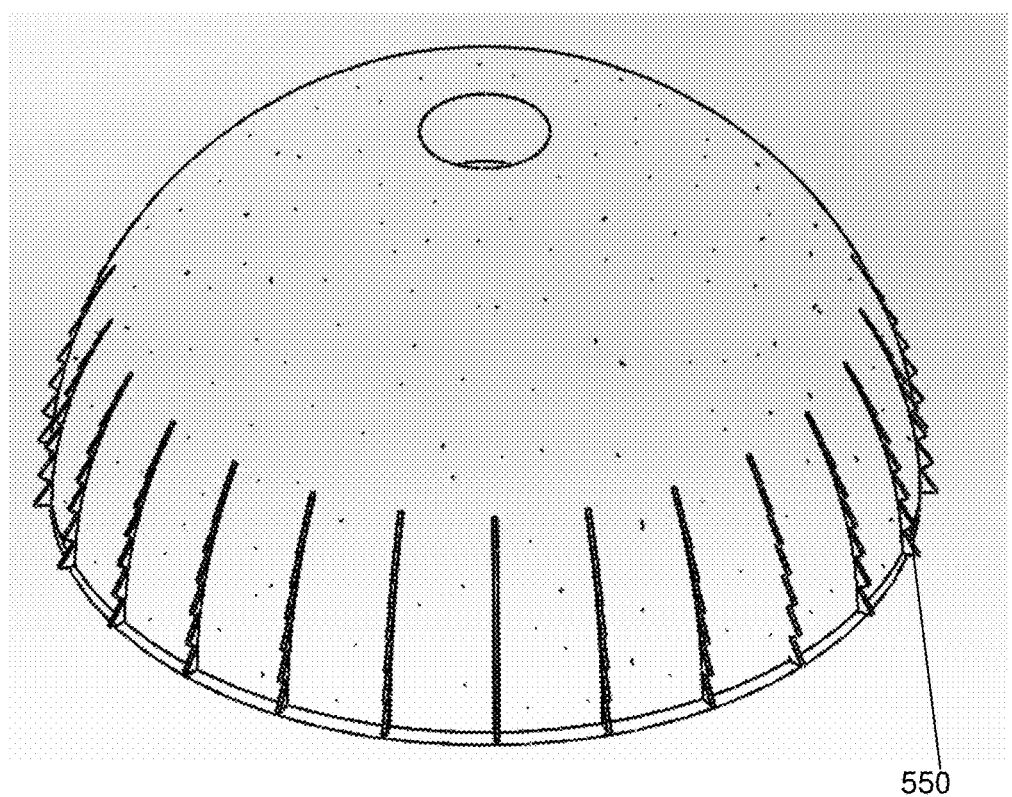
FIG. 6A is a three-dimensional view of a generally hemispherical external shape having fins that also have sawteeth on their exteriors.
Figure 6B:
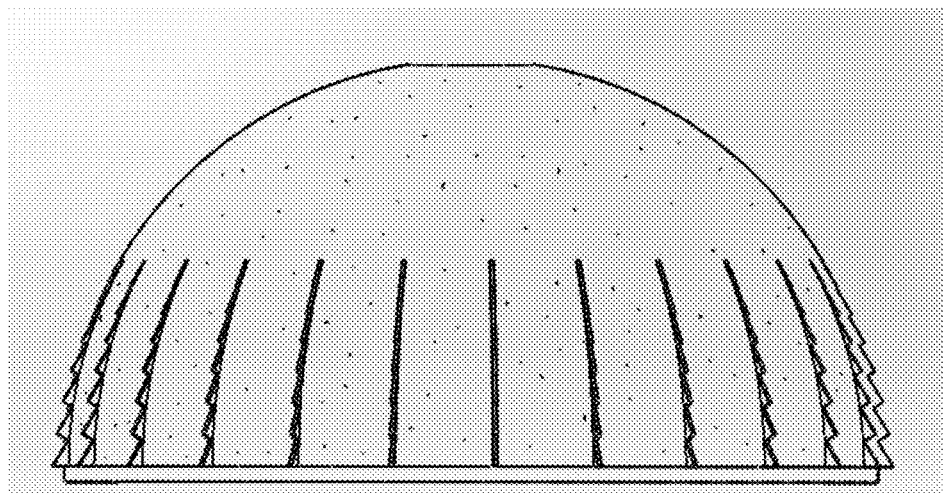
FIG. 6B is a side view of FIG. 6A.
Figure 6C:
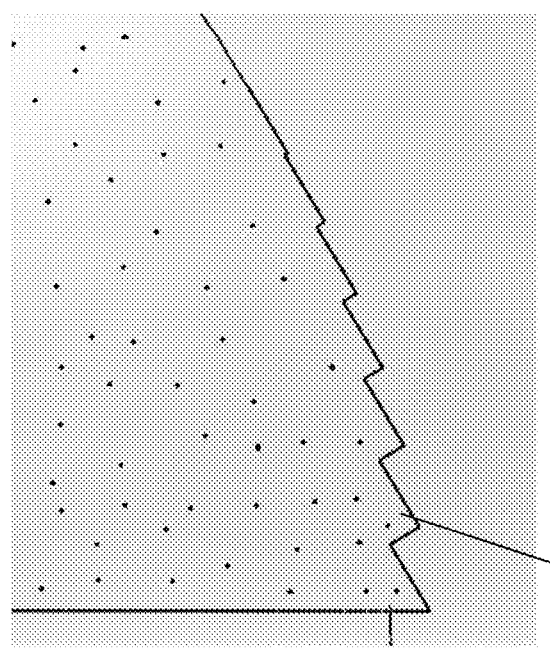
FIG. 6C is a side view of one fin of FIG. 6B, more closely showing the sawteeth.
Figure 6D:
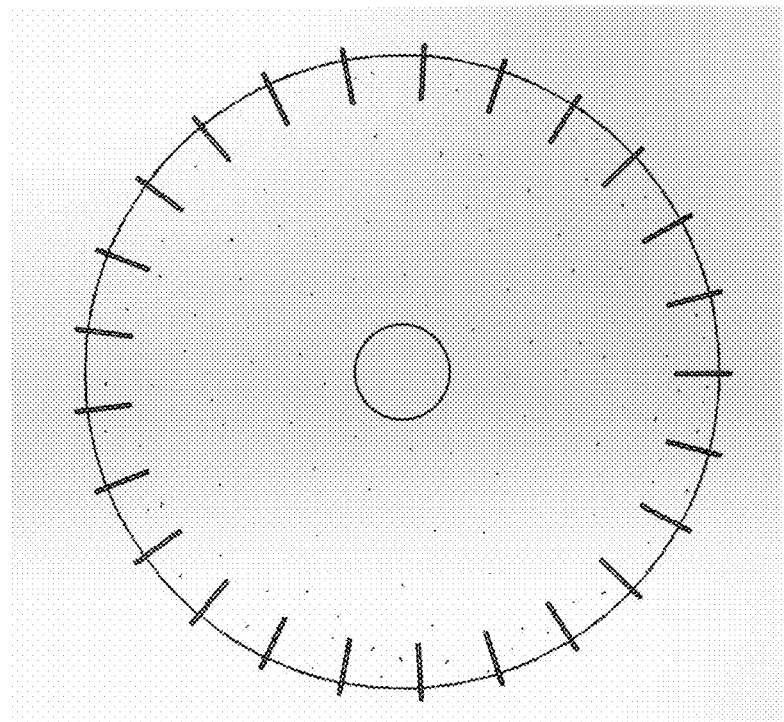
FIG. 6D is a top view showing just the placement of fins, without showing details of sawteeth.
Figure 6E:
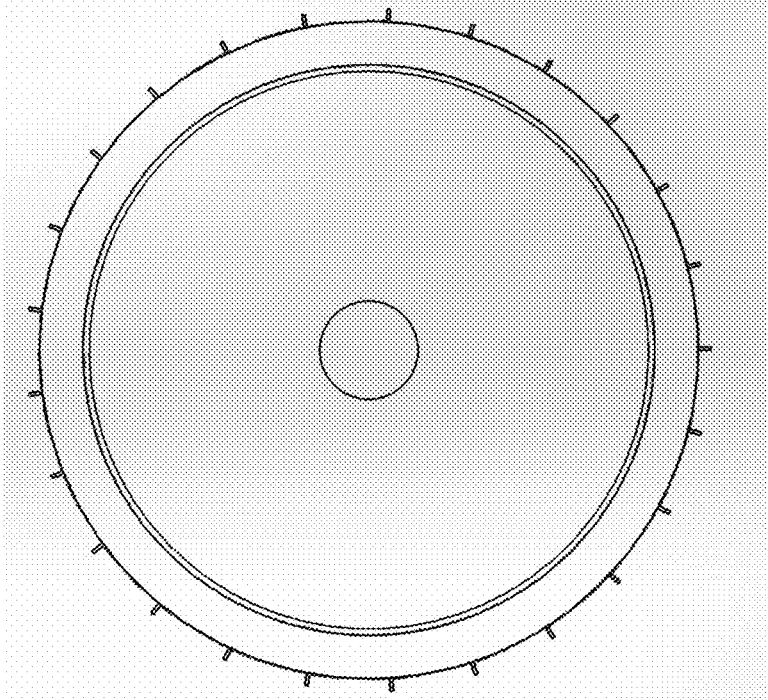
FIG. 6E is a bottom view showing just the placement of fins, without showing details of sawteeth.
Figure 6F:
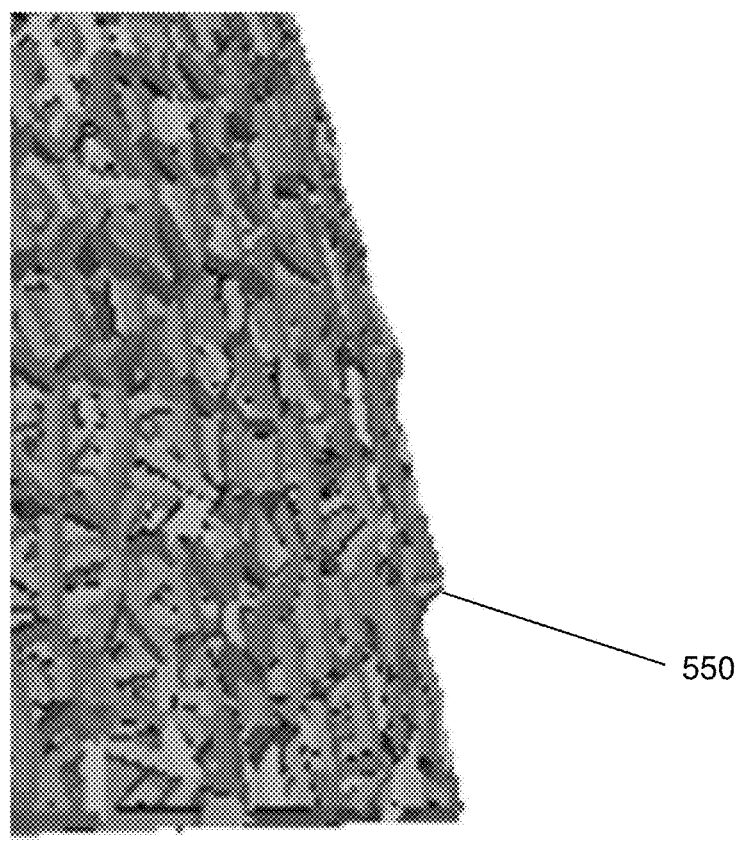
FIG. 6F shows a fin that has sawteeth and shows a plurality of interconnected struts that make up the fin and the sawteeth on the fin.
Figure 7A:
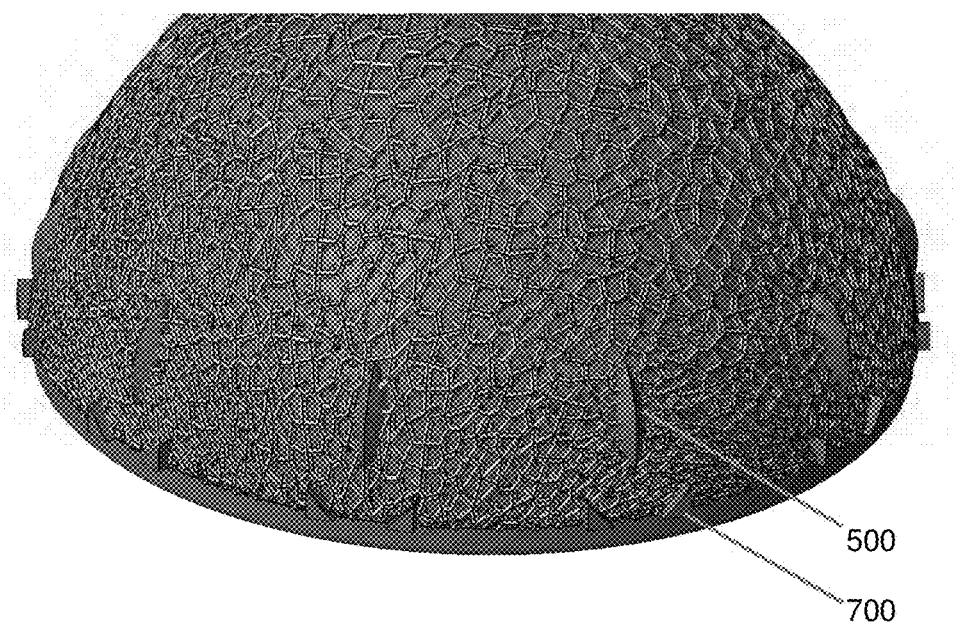
FIG. 7A is a perspective view of an embodiment having fins and divertor structures.
Figure 7B:
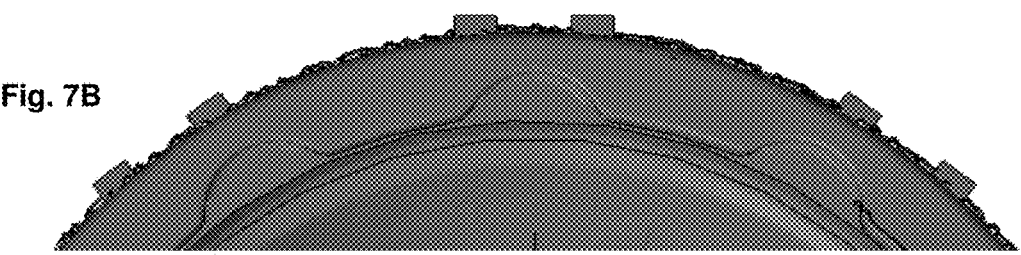
FIG. 7B shows a bottom view of an embodiment of the invention, having a generally hemispherical exterior shape and having both fins and divertor structures, with only the divertor structures being visible in the bottom view.
Figure 7C:
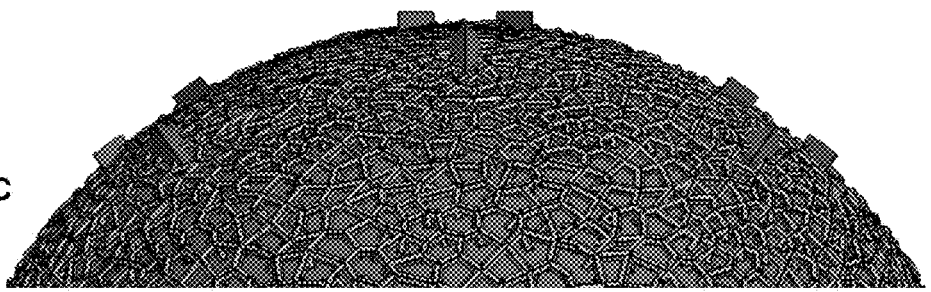
FIG. 7C shows a top view of the same embodiment.
Figure 7D:
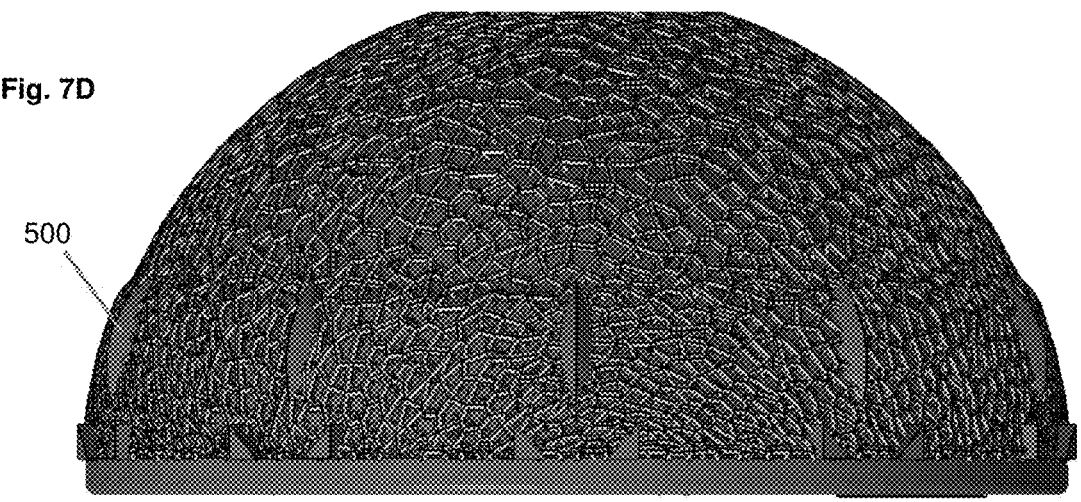
FIG. 7D shows a side view of a portion of a side view of the view of FIG. 7C.
Figure 7E:
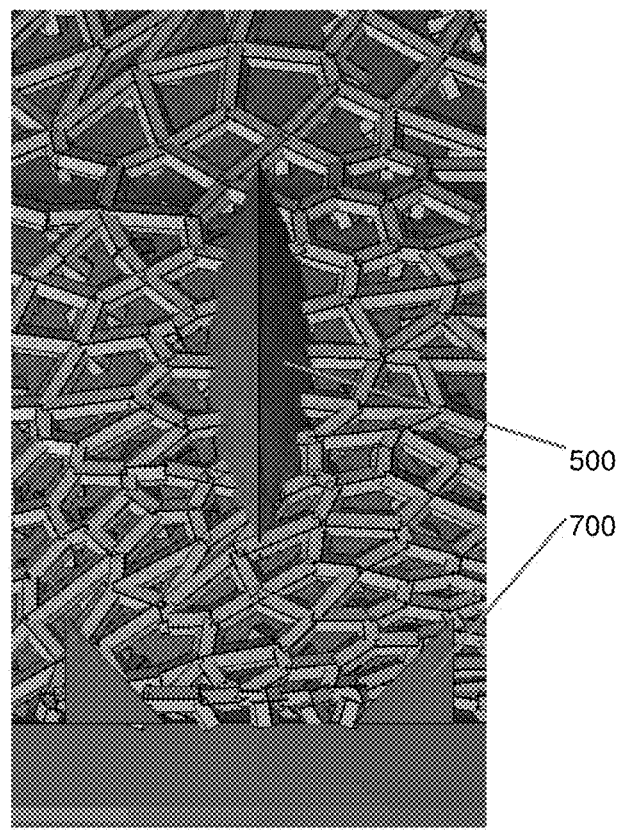
FIG. 7E is an enlarged view of the central portion of FIG. 7D.

In addition to the previously-described basic shape of a fin, and referring now to FIGS. 6A-6F, a fin sawtooth shape 550 may exist on an outward-facing surface of a fin 500. The fin sawtooth 550 may exist substantially all along an outward-facing surface of a fin 500, or it may exist only in some places, and its dimensions could vary as desired. If the implant 10 is at least approximately hemispherical on its exterior having a pole and an equator, the fin sawtooth feature 550 may exist primarily near the equator and might exist not so much or not at all in the polar region of implant 10. The fin sawtooth 550 could be made of an array of struts 300, or at least some of the fin sawtooth 550 could comprise an array of struts 300. The fin sawtooth 550 may have its tip, and may have a width, in an equatorial direction, that is at least one strut-length of a typical strut 300. The cutting edge of the tip of a sawtooth 550 could be a single strut 300 or a series of struts 300 that are approximately aligned with each other. FIG. 6F illustrates individual struts 300 making up the second region 200, the fin 500, and the sawteeth 550 on the fin 500.

As illustrated in FIGS. 6A-6F, fin sawteeth 550 are superimposed onto the external surface of a fin; however, more generally, such a tooth-like structure, either singly or in a series, could be superimposed onto any shape or portion of the implant 10.

As illustrated in FIGS. 6A-6F, a tooth 550 is essentially triangular when viewed from the side of the tooth, i.e., its external shape is made of straight-line segments. However, it is also possible that some of the shape of the edges or surfaces could be curved or other shape if desired. For example, teeth as found in certain animals can have a generally sharp tip while at the same time having some curvature in their overall shapes.

If there are successive teeth on a fin, the heights of various teeth, relative to the rest of the local surface, do not have to be constant or equal. Similarly, the distances of the tips of such teeth from a reference axis of the implant do to have to be constant or equal, either. For example, there may be a pattern of the heights of successive fins that may continuously vary along a given direction. Such a pattern may resemble the cutting tool known as a broach, in which each tooth extends farther out than a preceding tooth by a defined amount. Also, a fin with sawteeth could exist on a femoral stem, for example.

Divertor Structure

Reference is now made to FIG. 7A through FIG. 7E. It can be understood that if the fins 500 generally lie in respective planes that contain the axis of the direction of implantation of the implant 10 (such as if the fins 500 lie along lines of longitude using the analogy of the geography of the Earth, for situations in which the implant 10 is at least approximately hemispherical on its exterior), it is possible that the fins 500 could cut corresponding grooves into the natural bone as the implant 10 is advanced into place in a prepared socket in bone and the fins 500 pass through the bone. It may be considered (although it is not wished to be limited to this explanation) that the material of natural bone is somewhat malleable, able to be pushed around and reshaped to some extent by shapes and objects that exert force on the bone or advance through the bone. If, after implantation, the implant 10 has any tendency to back out, in a direction opposite to the direction of advancement during implantation, it is possible that those grooves formed in the bone, which might remain open after the fins 500 have passed along their insertion path, could possibly provide a path conducive to the backout motion of implant 10. Such backout motion would be undesirable.

To counteract this possible tendency, there may be provided provide additional structures on the implant 10, which may be called divertor structures 700. These divertor structures 700 may be located rearward of the fins 500 (with respect to the direction of motion for insertion of the implant 10 into bone), such as closer to the equator than the fins themselves. With respect to equatorial angle, the divertor structures 700 may be located between the fins 500 or, more generally, may be located so that they are not perfectly in line with fins 500 along the path of the fin 500. The divertor structure 700, when viewed along the lengthwise direction of fin 500, could overlap only partially with fins 500, or it might not overlap at all with fins 500. It is possible that divertor structure 700 could have a leading edge that is sharp. It is possible that the divertor structure 700 could have a trailing edge that is blunt. The location and shape of the divertor structures 700 may be such as to redirect bone material back into the grooves, in the bone, that the fins 500 have created by the forward motion of the implant 10 during its implantation. That rearranged bone material would partially block the groove that was just created by the passage of the fin 500. Such rearrangement of bone material may help to resist possible motion in which the implant 10 might back out if its implanted location by moving in a direction opposite to the direction of implantation of the implant 10, although it is not wished to be limited to this explanation. For implant 10 whose exterior is at least approximately a hemisphere, divertor structures 700 may be located close to the equator. It is possible that the fins 500 could end without extending all the way to the equator, and the divertor structures 700 could be located closer to the equator than the ends of the fins 500.

Similarly to other types of macroscopic surface-interrupting features 400 described elsewhere herein, the divertor structure 700 may be made of or can comprise an array of struts 300. The divertor structure 700 may have a dimension out of the surface of implant 10 that is at least one typical or average length of struts 300.

Alternatively it is possible, as illustrated in FIGS. 7A-7E, that a divertor structure 700 could be formed of solid or substantially-solid material like first region 100. Such a solid structure would interrupt the second region 200 of interconnected struts 300, exposing solid or substantially solid material to bone in some isolated places. The existence of solid or substantially solid material in such places may provide mechanical strength to the divertor structure 700. A divertor structure 700 is not the only localized shape that could be made of solid or substantially-solid material amongst or interrupting an array of interconnected struts 300. Similarly, fins 500, sawteeth 550, an engagement ridge 600, or generally any desired shape could be made of solid or substantially-solid material, even while other nearby portions of the surface comprise arrays of interconnected struts 300. In addition to acetabular cups, a femoral stem could have such a structure, and generally any other shape of implant could have such a structure.

Porosity, Pore Size, Average Strut Dimension, and Empty Volume Fraction

In general, two parameters that can describe a porous structure are porosity and pore size. In general, within any region of any size or shape that may be considered, porosity is the volumetric fraction representing the volume of empty space in the region compared to the overall volume of the region. Porosity is a fractional number between zero and one. For purposes of calculating porosity, in order for the calculated quantity to have a representative physical meaning, it is preferable that the region considered should be at least the size of one pore, and preferably, for statistical purposes, should contain a plurality of pores. Nevertheless, the region considered can be smaller than the entire implant 10; it is entirely possible to describe a local region by calculating a porosity for a local region that is only a portion of the entire porous region of the implant 10.

Pore size can be considered to be a characteristic dimension that represents or describes the empty space within a pore. If a cell or pore region is not spherical or symmetric or of uniform dimension, a representative pore size may be used that is an average of internal dimensions of a pore taken in multiple different directions, or is a dimension of a sphere having an equivalent volume equal to the empty space within the pore.

In an embodiment of the invention, for the described array of struts, internal dimension of polygons or polyhedra that make up the array of struts 300, as discussed elsewhere herein, may be chosen to be within a size range that is known to be conducive to bone ingrowth. The internal dimensions of polygons or polyhedra, or average lengths of struts, can be chosen to correspond to a pore size range that is conducive to bone ingrowth. The internal dimensions of the polygons may fall within a distribution of sizes. The local empty volume fraction of the region made up by interconnected struts can correspond to a porosity range that is known to be conducive to bone ingrowth. As a numerical example, in second region 200, the local empty volume fraction may be between approximate values of 30% and 70%. The characteristic dimension of an enclosed cell region formed by struts 300, which roughly corresponds to an average strut length, may range between approximate values of 0.1 millimeter and 1 millimeter. The average thickness of second region 200, measured from the interface between first region 100 and second region 200, to an external enveloping surface of second region 200, may range between approximate values of 0.5 mm and 1.5 mm.

If the implant 10 is an acetabular cup or has a geometry having any hemispherical external features, the implant 10 may be described as having an equator and a pole. The terms equator and pole are used by analogy to the geography of the Earth. Equator may correspond at least approximately to the equator of a hemisphere, but the interior of the implant 10 such as an acetabular cup need not be exactly or fully a hemisphere. For example, it is possible that the cup could go fully around the axis of revolution while occupying less than a full hemisphere, but for present discussion the word equator might still be used. More generally, the equator may be a path or band that goes substantially around a substantially axisymmetric external opening of the implant 10. With continuing analogy to the geography of the earth, it is possible that the acetabular cup could be a full hemisphere such as the northern hemisphere, occupying latitudes from 0 degrees (the equator) to 90 degrees (the north pole). Alternatively it is also possible that the acetabular cup could occupy latitudes such as from 10 degrees latitude to 90 degrees (the north pole), or as still another alternative the acetabular cup could even extend a few degrees beyond the equator into the southern hemisphere.

It is possible that at the equator, the average strut length (a linear dimension) can be smaller than it is at the pole. It is also possible that the local empty volume fraction of the region made up by interconnected struts (which is a fraction between zero and one) can be smaller at the equator than it is at the pole. Either of these could be true by itself, or both of them could be true simultaneously. This would be related to the fact that the typical positioning of an acetabular cup implant in bone is such that the equator of the implant is adjacent to cortical bone, which is relatively more dense and has a relatively smaller pore size, and the pole of the implant is adjacent to cancellous bone, which is relatively more porous having a relatively larger pore size. If there were a situation where the bone had opposite direction of how the porosity or pore size of the bone varied, or if something different were desired for any other reason, it would also be possible to provide the opposite trend of how the local empty volume fraction of the region made up by interconnected struts or the average strut length of the implant varied from the equator of the implant to the pole of the implant. The variation of the average strut length or the local empty volume fraction of the region made up by interconnected struts or both, in the second region 200, could exist in a stepwise manner. Yet another possibility is that between the equator and the pole of the implant, there can be a continuous variation or gradient of the local empty volume fraction of the region made up by interconnected struts, a continuous variation or gradient of the average strut length, or continuous variations or gradients of both of these quantities. It is still further possible that there could be a continuous variation of one of those parameters in combination with a stepwise variation of another of those parameters. In a device that has an axis of revolution, the distributions of these local parameters can be axisymmetric, although they do not have to be. The function that describes this variation of average strut length does not have to be the same as the function that describes the variation of local empty volume fraction of the region made of interconnected struts. For example, one of these variations could be linear while the other could be some other function. The starting or ending points of these variations could be different.

Yet another possible variation would be to vary the thickness or cross-sectional area or shape of the struts from one place to another in the implant, to the extent that such variation is permitted or achievable by the manufacturing process.

Any of these described features such as engagement ridges, fins, crests, teeth, macroscopic surface-interrupting features, concavities and convexities, and divertor structures, could have within them variations of local average strut length or local empty volume fraction or both as just discussed for the implant in general. Such variations could be stepwise variations or continuous variations as desired. For example, the variation could be such as to place, in a region of the implant 10 that would abut cortical bone, an array of interconnected struts that has smaller average strut length or smaller local empty volume fraction or both, than in some other part of the implant 10. Similarly, the variation could be such as to place, in a region of the implant 10 that would abut cancellous bone, an array of interconnected struts that has larger average strut length or larger local empty volume fraction or both, than in some other part of the implant 10. Such variation could be present in the concavities or the convexities or both, or generally in any local feature that may exist in or on the implant 10.

Tapered Struts

Figure 8A:
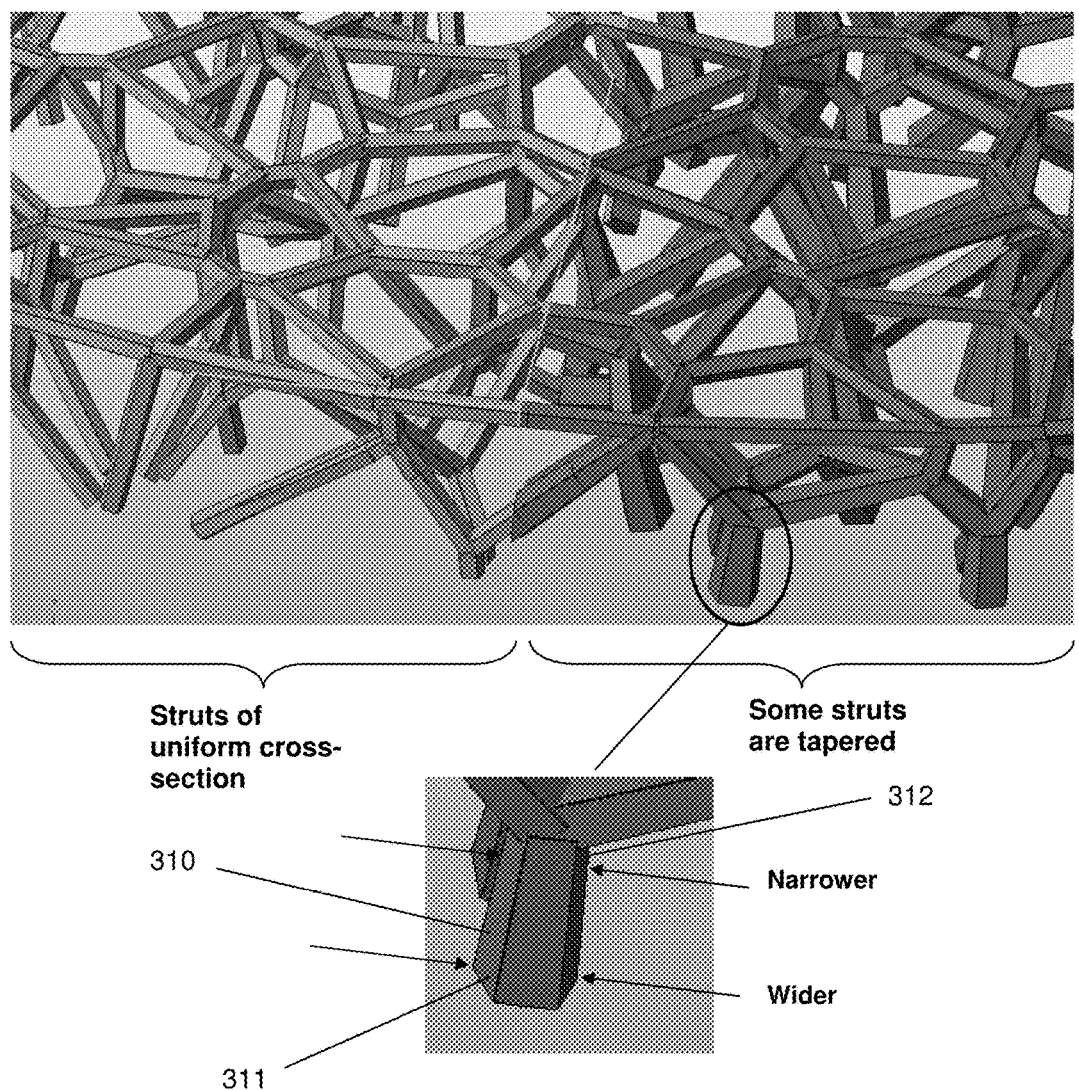
FIG. 8A is a three-dimensional perspective view of an array of interconnecting struts in which, on the left, the struts are of constant cross-section along their length, and, on the right, some of the struts are tapered along their length.
Figure 9:
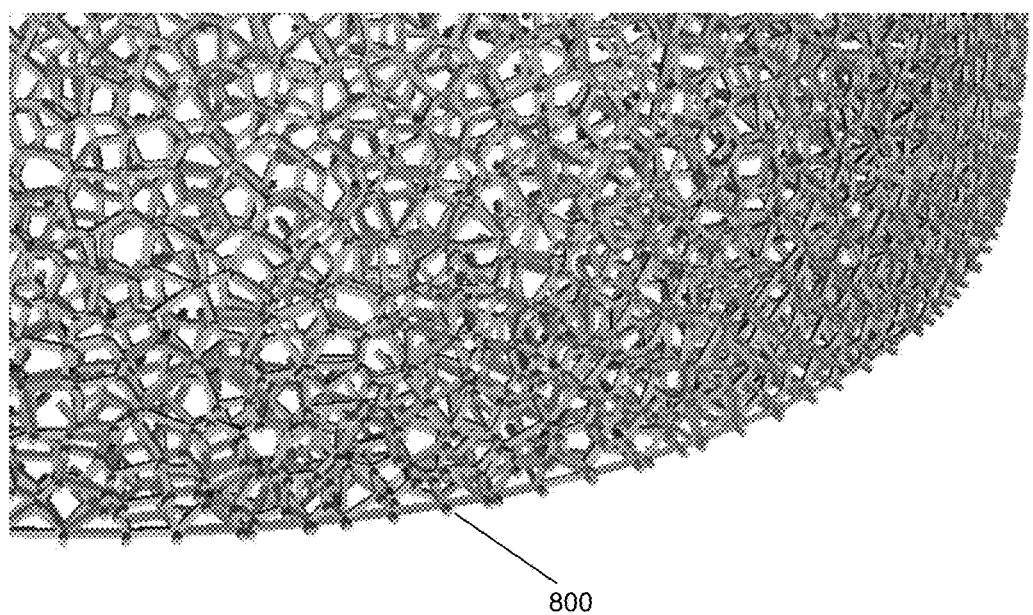
FIG. 9 is an external view, generally along an axis, showing the level of detail of individual struts, both exterior and interior, of an implant that has cantilevers on the exterior. This is a view of the mesh structure, with the solid interior omitted for clarity of illustration.

In an embodiment of the invention, there may be provided struts whose cross-sectional area varies as a function of position along the length of the strut. FIG. 8A-8C show an array of interconnecting struts in which, for purposes of illustration only, in one half of the illustration, the struts are of constant cross-section along their length, and, in the other half of the illustration, some of the struts are tapered along their length. In FIG. 8A, as well as in FIG. 8C, the bottom edge of the array of struts is where the struts would connect to the solid or nearly-solid first region 100. For clarity of illustration, this region 100 is not shown. In FIGS. 8A-8C, the tapered strut is labeled as tapered strut 310. The larger-cross-section end is 311, and the smaller-cross-section end is 312. In the tapered illustrations in FIGS. 8A-8C, not all of the struts are tapered. The struts close to the solid or nearly-solid first region 100 are shown as being tapered, while the struts further away in that same array are shown as being untapered.

FIG. 8A is a three-dimensional perspective view. In this illustration, the left side of the illustration shows untapered struts, and the right side shows some tapered struts. For the tapered struts, the larger-cross-section end 311 of the strut is toward the bottom of the illustration, which is adjacent to the solid or nearly solid first region 100.

FIG. 8B is a top view. The untapered situation is in the left half of the illustration and the tapered situation is in the right half of the illustration. In the appropriate half of FIG. 8B, the tapered struts 310 are in the background of the illustration. The larger-cross-section end 311 of the strut would be further to the background than the smaller-cross-section end 312. The solid or nearly solid first region 100, if it were shown, would be even further in the background.

FIG. 8C is a side view. In this illustration, the left side of the illustration shows untapered struts, and the right side shows some tapered struts. For the tapered struts, the larger-cross-section portion of the strut is toward the bottom of the illustration. In these Figures, for clarity of illustration, the solid or nearly solid region is not shown. In FIGS. 8A and 8C, the solid or nearly solid region would be at the bottom of the illustration. In FIG. 8B, the solid or nearly solid region would be in the background.

As illustrated, in this situation, the larger-cross-section portion of the strut is closer to the solid or nearly-solid region, which is first region 100. It is believed, although it is not wished to be limited to this explanation, that such tapering may provide a sort of transition from the high rigidity of the solid or nearly-solid region (first region 100) to the lesser rigidity of the second region 200 (the array of interconnected struts 300). The second region 200 has lesser rigidity at least because of its open space. By virtue of the tapering of some of the struts, the change in stiffness is not as sudden as it otherwise would be, but instead can be more gradual. It is believed, although again it is not wished to be limited to this explanation, that such a transition may improve load transfer between the first region 100, the struts 300, and eventual ingrown bone. It is believed that this may improve on a situation that could be considered to be analogous to a stress concentration factor in more classical forms of solid mechanics. As a non-limiting example, the total included angle of taper of a tapered strut 310 may be several degrees. Tapering of tapered struts 310 may contribute to a gradual change of local empty volume fraction within second region 200.

Cantilevers

As described elsewhere herein, an embodiment of the invention may have a surface-mesh, such that a mesh may approximately conform to a desired overall surface shape and may be filled with polygons or surfaces of polyhedra formed by struts 300.

In another embodiment of the invention, and referring now to FIGS. 9-12, there may be a surface mesh that approximately conforms to a nominal surface as just described but, in addition, at at least some of the vertices on the surface, there may be a cantilever 800 extending generally outward away from the implant 10 without connecting further to any other vertex or structure. A cantilever 800 may be considered to be a structure resembling a strut in its dimensions and general appearance, and may be manufactured by the same process as struts. However, in contrast to struts, which would join other struts at both ends of the strut, a cantilever may be connected to other struts or structure at only one of its ends. The cantilever 800 may extend out unsupported, from the vertex or structure to which it is connected. The cantilever 800 may extend out for a distance that is comparable to or less than the typical or average length dimension of struts 300 in the mesh. The tip of the cantilever 800 farthest from the implant 10 may be either sharp or blunt to any desired degree. In general, such cantilevers 800 could be thought of as resembling the thorns that are found on some plants, the barbs on some fishhooks, or porcupine quills. Shapes and features such as fins, engagement ridges and sawteeth, discussed elsewhere herein, may be on a slightly larger dimensional scale than cantilevers, and may be made of pluralities of struts. However, as discussed herein, it is also possible for features such as fins, engagement ridges and sawteeth to comprise cantilevers on their exteriors.

A cantilever 800 may have a generally lengthwise direction having an orientation. One possibility is that cantilevers 800 could be generally perpendicular to the local surface. Another possibility is that cantilevers 800 could be directional extensions of struts that already exist near the surface of implant 10 and that join the same vertex as those struts. Still another possibility is that the cantilevers 800, or at least some of them such as a majority of them, may point generally rearward with respect to the direction of motion for the implant 10 to be advanced into its implantation site in the patient's body. The outward-pointing cantilevers 800 can (at least most of them) be angled at an angle similar to each other, not perpendicular to the local surface and not a simple extension of a mesh, but rather so as to provide a preferred insertion direction of the implant 10 and so as to have resistance to reverse motion of the implant 10 in a direction that is opposite to the preferred insertion or advancement direction of implant 10. For the various cantilevers 800, the angles of individual cantilevers 800 could be at a defined angle relative to the axis of revolution of the implant 10, or could be parallel to the orientations of other cantilevers 800, or could be at a defined angle relative to the local surface tangent of the implant 10, or could have any other desired definition or constraint. For an implant 10 that has an external shape that is at least approximately hemispherical, it is possible that at least some, or all, of the cantilevers 800 could point toward the equator. Cantilevers 800 in different locations could point in various different directions if desired.

Also, as illustrated, for a geometry of an acetabular cup or similar generally hemispherical shape, it is possible that these cantilevers 800 may be provided in regions at or near the equator of the implant 10, but they may be absent or less common at or near the pole of the implant 10. More generally, it is possible for there to be a greater number or number per unit area of cantilevers 800 at or near the equatorial region, compared to at or near the polar region. In general, cantilevers 800 may be placed at substantially all vertices within a local region, or may be placed at less than all of the vertices within a local region. Of course, the dimensions of individual cantilevers 800 can also be varied as may be desired. A cantilever 800 could be tapered if desired, similarly to struts 300. For example, a cantilever 800 could have a larger cross-section near its joined end and a smaller cross-section near its cantilevered end.

Cantilevers 800 can exist on some portion of the majority surface, or all of the majority surface. The locations in which cantilevers 800 are provided can be selected by angular position with respect to a polar angle, or by angular position with respect to an azimuthal angle, or by some combination of polar angle and azimuthal angle.

It is believed, although it is not wished to be limited to this explanation, that such cantilevers 800 may improve initial mechanical fixation of the implant in its intended implantation site, especially at and shortly after the time of surgery, before bone ingrowth and healing has occurred.

Such cantilevers 800 may also be used for other shapes of implants other than the illustrated generally hemispherical implant. For example, such cantilevers 800 may be placed on a stem such as a femoral stem, or in general any stem that is intended to go into a canal of a long bone. Cantilevers 800 may be placed on a flat surface, or on a curved surface of any curvature. In any such usage, cantilevers 800 may be placed where the surface tangent of the external surface of the implant 10 is approximately parallel to or is at a shallow angle relative to the direction of motion for implantation, and cantilevers may be absent where the local surface tangent of the external surface of the implant 10 is relatively closer to perpendicular to the direction of motion of the implant 10 for implantation. It is believed, although it is not wished to be limited to this explanation, that cantilevers where the surface tangent is approximately parallel to or is at a shallow angle relative to the direction of motion for implantation are better able to dig into the bone to resist backing-out of the implant because backing-out motion would cause them to dig into bone such as to resist further backing-out.

Cantilevers 800 can be on a macroscopic surface-interrupting feature 400, although they do not have to be. For example, cantilevers 800 may be placed on a macroscopic surface-interrupting feature such as a fin 500. Cantilevers 800 might be placed on some portion or surface of a macroscopic surface-interrupting feature 400 while being absent from some other portion or surface of the macroscopic surface-interrupting feature 400. Placement can be on a side surface while being absent on a radially-facing surface, or vice versa, or can be on some portion of sawteeth 550 while being absent from other portions of sawteeth 550. Cantilevers 800 can be placed on the peaks of a peak-and-valley type of surface such as is discussed elsewhere herein. Of course, cantilevers can also be placed on the majority external surface shape. Cantilevers could be placed on substantially all of the surface vertices in a local region, or at fewer than all of the surface vertices.

Figure 10B:
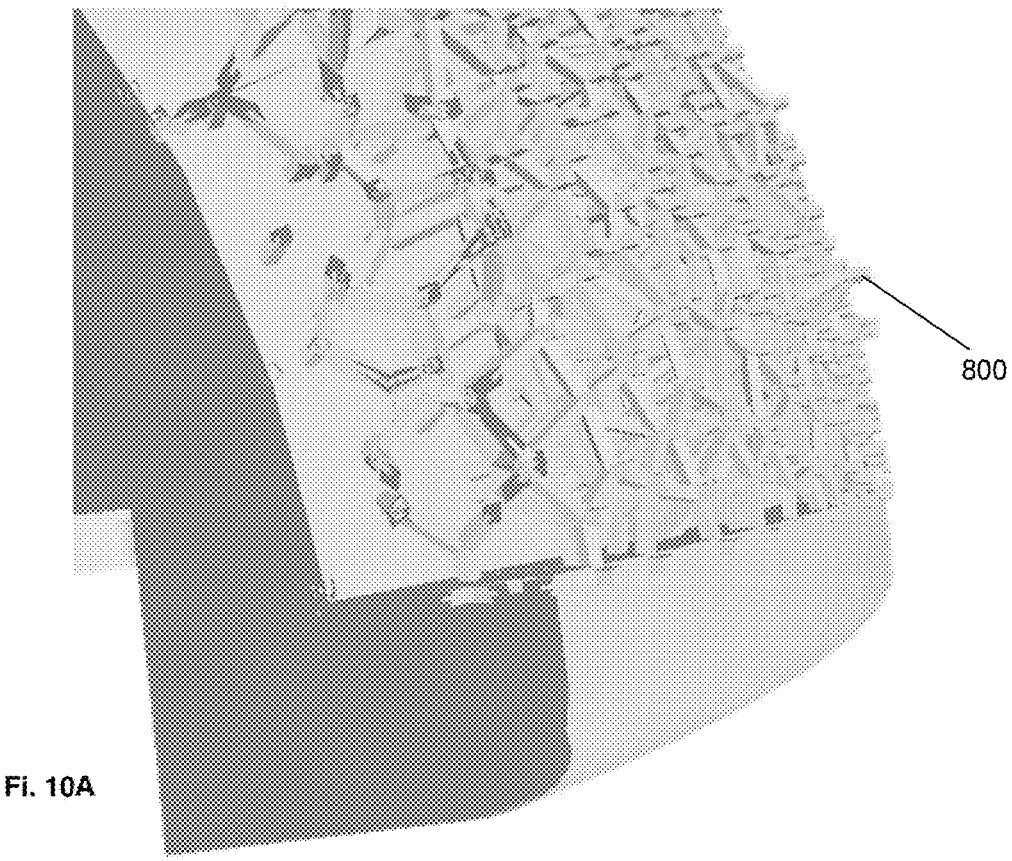
FIG. 10B is a schematic illustration of cantilevers on a generally hemispherical shape, wherein the cantilevers point generally backward with respect to the direction of insertion of the implant, toward an equator of the implant.
Figure 10B:
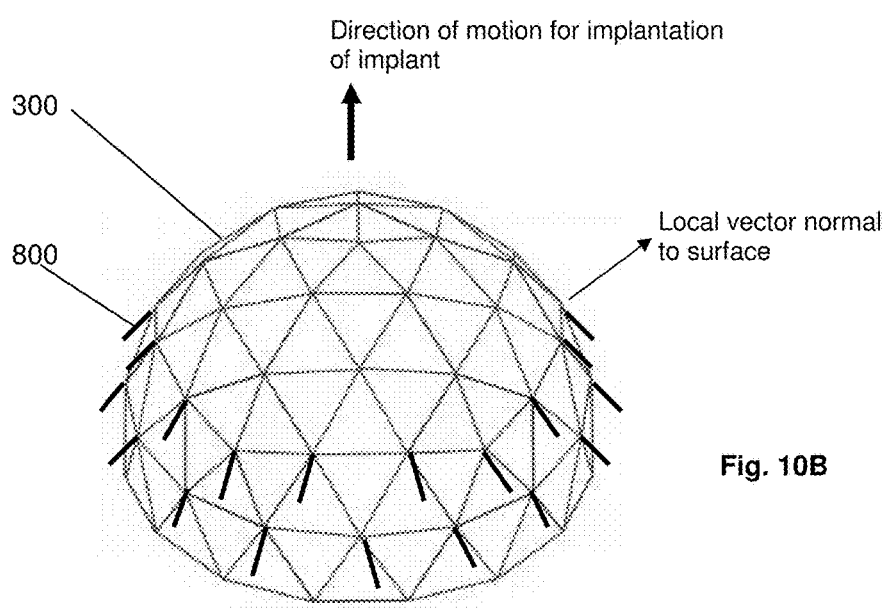
Figure 11:
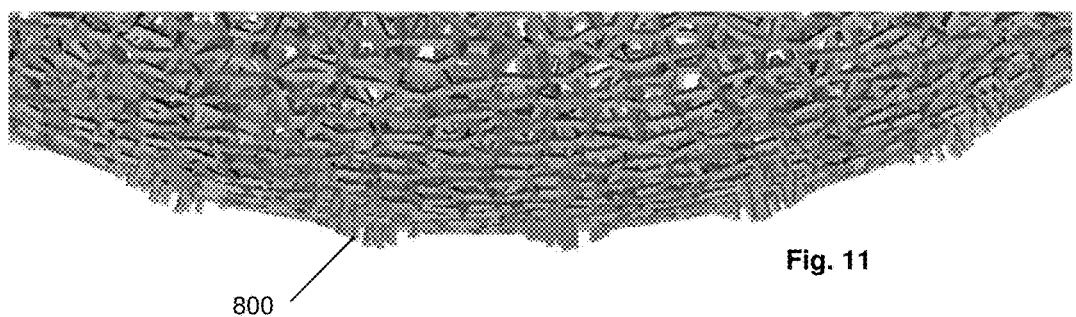
FIG. 11 is an illustration of cantilevers on fins, at the level of detail of showing individual struts.
Figure 12:
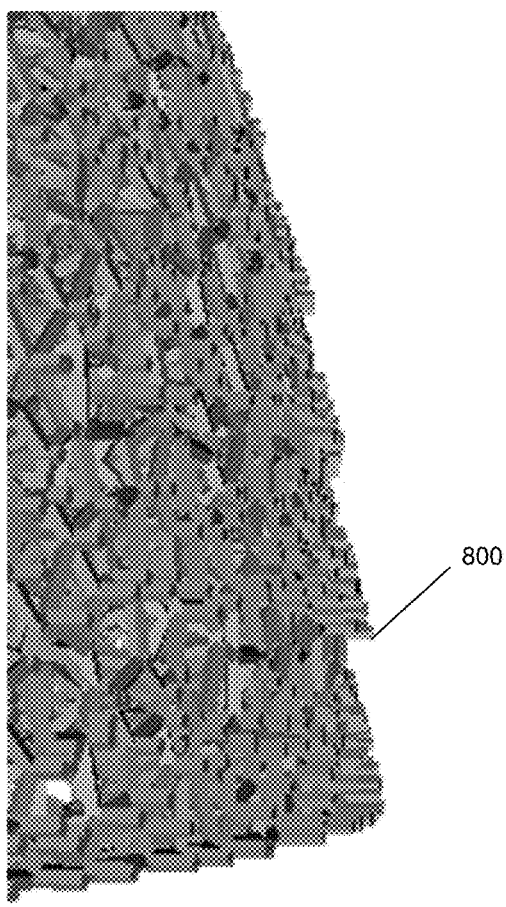
FIG. 12 is an illustration of cantilevers on sawteeth, at the level of detail of showing individual struts.

FIG. 10A shows an external view of an acetabular cup, sectioned, showing a first region 100 and also showing a second region 200 that contains interconnected struts. FIG. 10A also shows, visible especially against the background of the illustration, cantilevers 800. Although some of the cantilevers 800 in FIG. 10A appear to be perpendicular to the local external surface (i.e., parallel to the local normal vector), it is also possible that some or all of the cantilevers could be pointed in specific directions as discussed herein. FIG. 10B, using a much coarser schematic of the network of interconnected struts, shows that the cantilevers 800 can be angled so that they point rearward with respect to the direction of motion for implantation of the implant. FIG. 10B also illustrates placement of the cantilevers 800 preferentially near the equator of the approximately hemispherical external shape of the implant. FIG. 10B is only a schematic illustration in the sense that the number of struts is far fewer than would be found on an actual implant 10. FIG. 11 shows fins or crests, similar to FIG. 5B, but cantilevers 800 are additionally shown. The cantilevers 800 on the fins 500 or crests could be pointed in any desired direction, as discussed herein with respect to cantilevers 800 in general. FIG. 12 shows a sawtooth feature similar to FIG. 6, but cantilevers 800 are additionally shown. The cantilevers on the sawteeth could be pointed in any desired direction, as discussed herein with respect to cantilevers in general. It is possible that the overall external shape of sawteeth could be defined by an enveloping shape of cantilevers 800. It is possible that the overall external shape of features such as convexities, fins, teeth, crests, an engagement ridge, or any other feature could be defined by an enveloping shape of cantilevers 800.

Making a Designed Shape Out of the Envelope of the Cantilevers

Embodiments of the invention have described herein containing an array of interconnected struts such that an envelope of the array of interconnected struts forms a desired macroscopic shape. However, there is also another possibility for forming an enveloping shape.

In embodiments of the invention, it is possible that cantilevers 800 can be located and designed such that an envelope of the tips of the cantilevers forms a desired macroscopic shape. It is possible that various different cantilevers have different lengths, or different orientations, or both. Such variation can result in an enveloping shape that is defined by the tips of the cantilevers. Such variation can be designed into the implant by virtue of the programmed nature of the positional definition of the position of each strut 300 and cantilever 800.

Referring now to FIG. 12, there is illustrated a situation in which the tips of the cantilevers have an external envelope that has the shape of a sawtooth. More generally, any desired enveloping shape could be created. It is possible that the underlying array of interconnected struts could have a shape that is roughly similar to the enveloping shape of the tips of the cantilevers. Alternatively, the underlying array of interconnected struts need not have any particular relation to the enveloping shape of the tips of the cantilevers.

Distribution of Locations and Orientations of Cantilevers

In general, a cantilever 800 has two ends, i.e., a joined end and a cantilevered end. The joined end is where the cantilever 800 joins something else such as a vertex of other struts 300 or alternatively a solid region 100. The cantilevered end simply ends without being joined to anything else. A cantilever 800 may also be described by its orientation. The orientation of the cantilever 800 is the orientation of the line connecting the joined end to the cantilevered end.

In embodiments of the invention, it is possible that the location of the joined end may be distributed with some randomness, while the orientations of the cantilevers either may have some randomness or may be non-random. Alternatively, it is possible that the location of the joined end may be distributed in a non-random pattern, while the orientations (angular direction) of the cantilevers 800 either may have some randomness or may be non-random. The lengths of cantilevers could be random or could be designed.

Cantilevers that Directly to Join Solid Region

Cantilevers 800 have been discussed herein as being connected to a vertex where a plurality of struts 300 come together at a vertex.

Alternatively, in an embodiment of the invention, there may be provided an implant 10 such as an acetabular cup that has a first region 100 of solid or substantially solid material that appears on its external surface of the implant 10, to which are connected a plurality of cantilevers 800 projecting from the first region 100 of substantially solid material.

In an embodiment of the invention, an acetabular cup may have a band of substantially solid material on its external surface adjacent to a corner or edge. In such an acetabular cup, such a band may be adjacent to the equator of the acetabular cup. For example, such an feature may be provided based on the expectation that the edge of the acetabular cup not only might interface with adjacent bone of the acetabulum, but also might be slightly exposed to or adjacent to other types of tissue, which could be soft tissue that could possibly be irritated by irregularities at the edge of the implant. Accordingly, such band may be devoid of the interconnected struts 300 that are described and illustrated elsewhere herein. However, in this embodiment of the invention, referring now to FIGS. 13A-13C, there may be provided an implant that comprises a substantially solid region to which are connected a plurality of cantilevers projecting from a portion of the band.

Figure 13A:
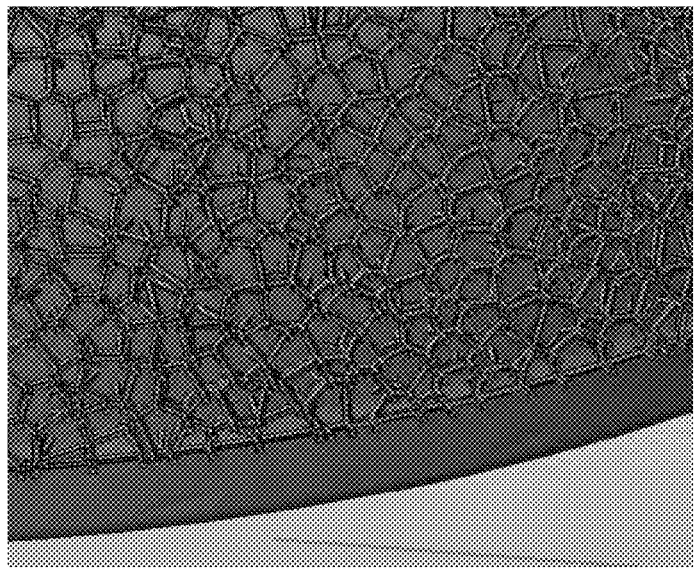
FIG. 13A is an illustration of cantilevers joining to an equatorial band solid region at the edge of the strut-containing region.
Figure 13B:
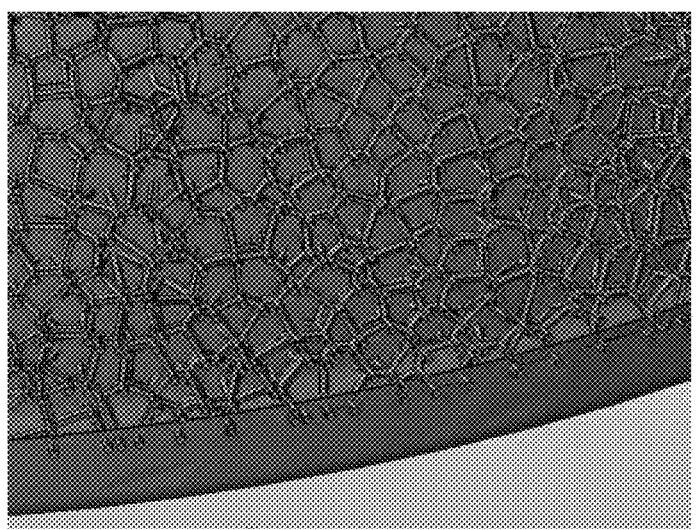
FIG. 13B is an illustration of cantilevers extending from a small portion of an equatorial band solid region.
Figure 13C:
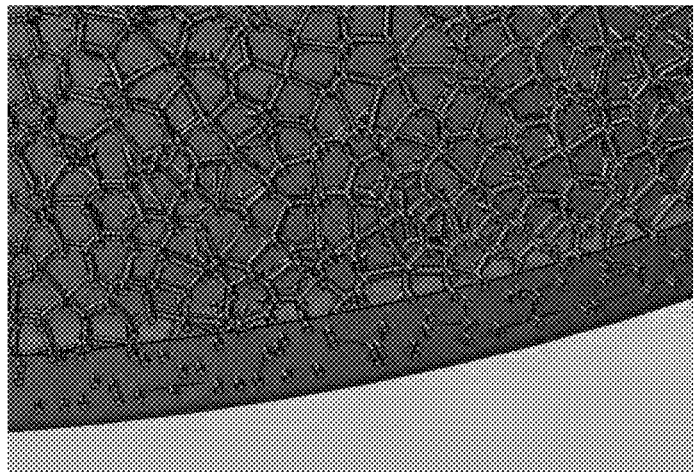
FIG. 13C is an illustration of cantilevers extending from most of an equatorial band solid region.

The cantilevers 800 could join the substantially solid region 100, such as the solid band, at locations that are distributed with some degree of randomness. The distribution and the randomness may be as described elsewhere herein. Alternatively, the orientation of the cantilevers where they join the substantially solid region may be random or may have a pattern. In FIG. 13A, such cantilevers 800 are shown projecting only up to the edge of the second region 200 that also contains interconnected struts 300. In FIG. 13B, such cantilevers 800 are shown projecting from the solid band of region 100 in a row that remains some distance away from the equatorial edge of the acetabular cup. In FIG. 13C, such cantilevers 800 are shown projecting from most of the region 100 solid band of the acetabular cup.

In FIGS. 13A-13C, the cantilevers are shown as projecting approximately perpendicular to the equatorial band, but of course they could project at any desired angle.

Cantilevers that are Non-Straight, Such as Bent

Figure 14:
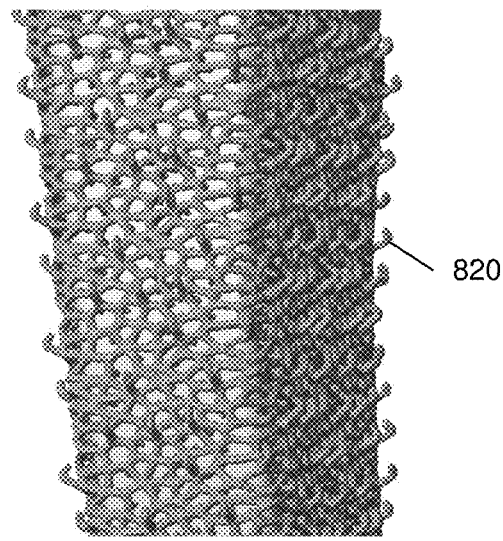
FIG. 14 is an illustration of cantilevers that are bent.

In an embodiment of the invention, there may be provided cantilevers that are not completely straight. For example, such a cantilever could be curved, or such a cantilever may comprise a first straight segment followed by a second straight segment that is not aligned with the first straight segment. Such two-straight-segment cantilevers 820 are illustrated in FIG. 14.

Such a two-straight-segment cantilever could be described as having a vertex that is formed by the junction of only two struts. Such a vertex may occur only on the outside of the second region 200, i.e., away from the first region 100 that is solid or substantially solid. As with other described cantilevers, such cantilevers 820 may be bone-facing. Such cantilevers can extend in random directions, or can extend backwardly. Such cantilevers could be present in some zone of the second region 200 and absent in another zone of the second region 200. Such cantilevers could have lengths that are random, or else have a designed pattern. Such cantilevers could have ends that form a desired enveloping shape.

Cantilevers of the non-straight variety can be oriented radially outward, or could be oriented in a particular orientation, or oriented in a particular plane, or could be oriented with some amount of randomness. The overall lengths of these non-straight canatilevers could be uniformed, or random, or patterned according to an algorithm. Such cantilevers could be provided in some places and not in other places.

Loop Structure

Figure 15:
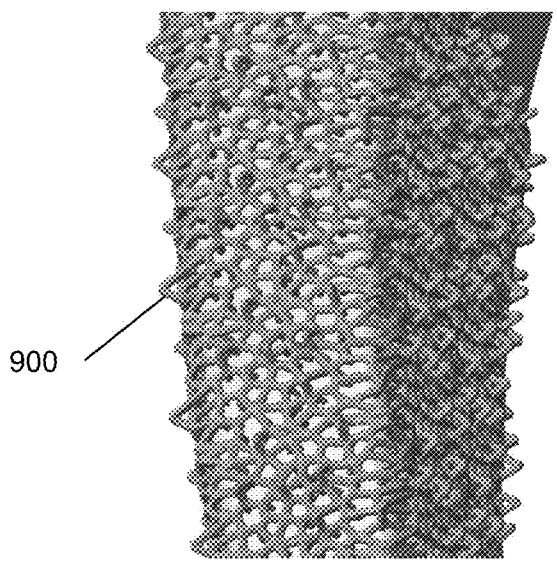
FIG. 15 is an illustration showing loop structures.

In an embodiment of the invention, there may be provided a structure that forms a loop structure 900. The term loop structure is used herein to refer to a non-straight element that is joined at one end to some other structure and joined at another end to some other structure. The loop structure 900 may be curved or may comprise a series of straight-line segments. Such a loop structure 900 is illustrated in FIG. 15. It could be described as having a vertex that has only two struts connecting at such a vertex.

In an embodiment of the invention that comprises a network of interconnected struts, the loop structure 900 may be provided only at a surface of the implant rather than amongst the network of interconnected struts 300 in the interior of the network. Such a surface that has loop structures 900 may, for example, be intended to be bone-facing. It would also be possible to provide loop structures that attach directly to a solid or nearly-solid structure such as first region 100. Properties such as orientations and lengths of loop structures could be uniform, random, or patterned. Loop structures could be provided in some places and not in other places.

Surgical Tooling and Interference

In an embodiment of the invention, it is possible that the dimensions of an implant 10 and the dimensions of surgical preparation tooling such as reamers could be coordinated such that there is an intentional mismatch between the dimensions of the preparation tool (reamer) and the dimensions of the implant 10, resulting in an interference fit of the implant in the prepared bone. Further, in connection with this, the surface of the implant 10 that faces the bone and experiences the interference fit could be an array of interconnected struts 300. It is further possible that there could be cantilevers 800 or loop structures 900 or both on the surface or a portion of the surface that is involved in the interference fit, as described elsewhere herein.

Other Shapes of Implant

Figure 16:
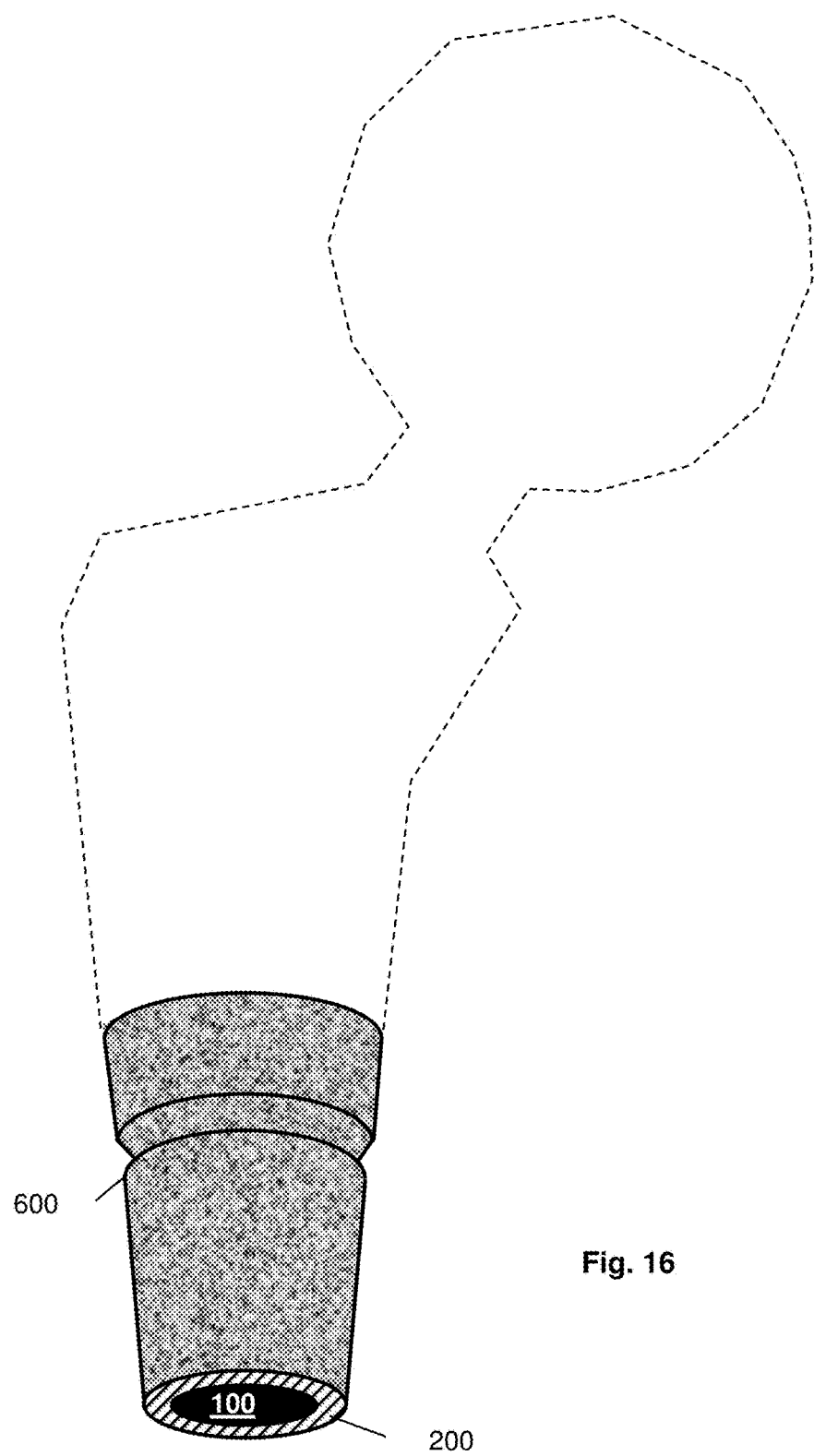
FIG. 16 shows a stem geometry having an engagement ridge.
Figure 17B:
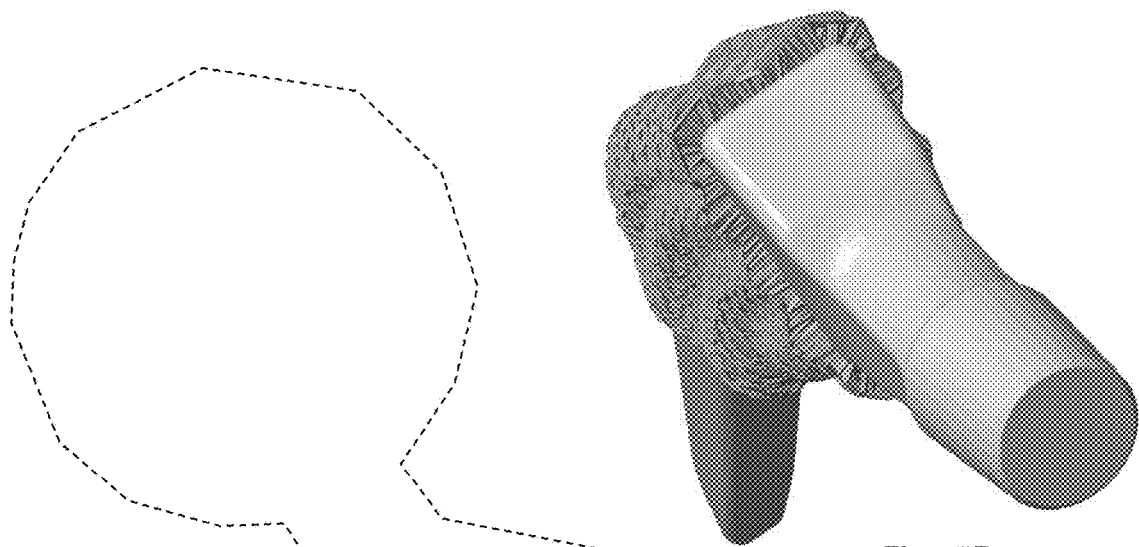
FIG. 17B shows a stem geometry having periodic crests around its perimeter, formed from an array of interconnected struts.
Figure 17A:
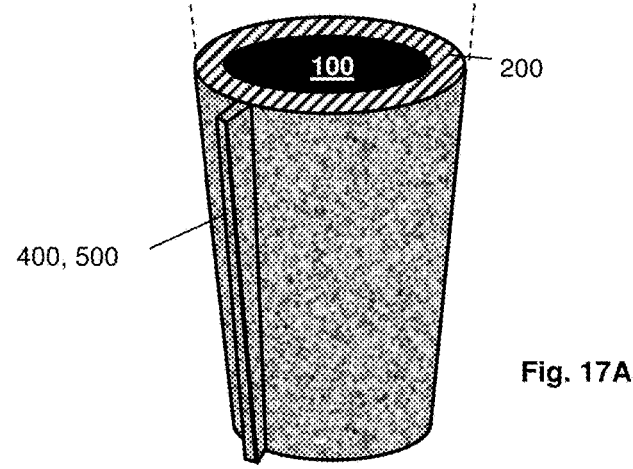
FIG. 17A shows a stem geometry having a fin.
Figure 17C:
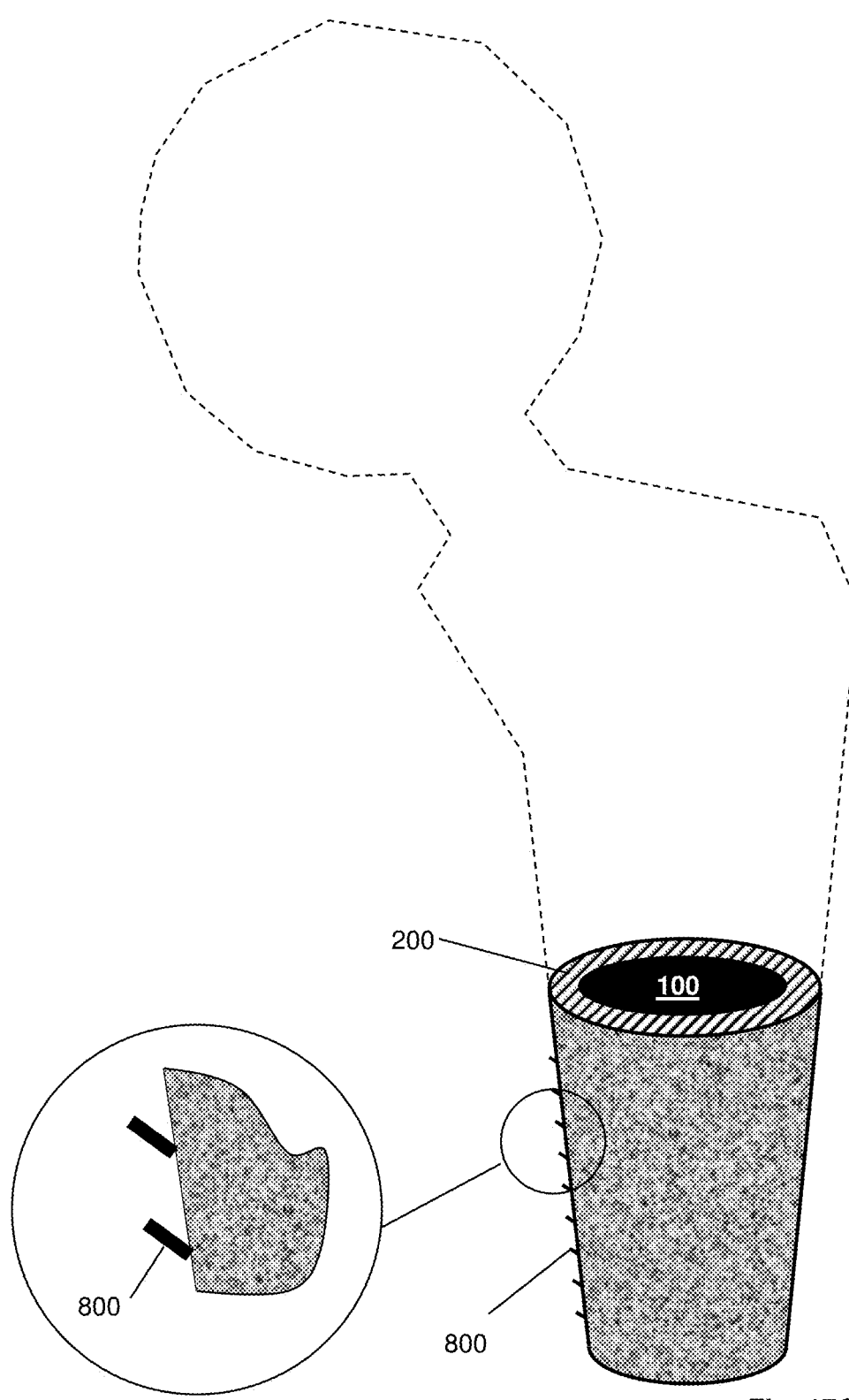
FIG. 17C shows a stem geometry having cantilevers.

Referring now to FIGS. 16-17D, there is shown the possible use of features mentioned herein with implants that may have a generally long shape rather than a hemispherical or nearly-hemispherical shape. These illustrations show portions of a shape that is elongated and frustoconical with a gentle taper. FIG. 16 shows an implant having an engagement ridge. FIG. 17A shows an implant having a fin. FIG. 17B illustrates an implant similar to that of FIG. 17A, but showing the array of struts. FIG. 17C shows an implant having cantilevers. In these illustrations, only a few instances of respective features are shown, for clarity of illustration. Only a portion of the length of the stem is shown, for clarity of illustration. The stem is shown as being frustoconical with a slight taper, but other shapes or tapers are also possible. Of course, any of these features could be used together with any others, in any combination. Such a shape could be a stem that is suitable to fit into the intramedullary canal of the femur for use in a hip replacement, or generally could be made such as to fit into the intramedullary canal of any long bone. For example, the device could alternatively be an intramedullary rod or intramedullary nail such as can be used for fracture fixation. The device could be at least partially cylindrical instead of the illustrated frustoconical shape, or could be still other shapes.

It can be appreciated that features described herein may be designed and manufactured into or onto generally any type of implant, such as any type of bone-facing implant. For an implant that receives a spherical component, the outside or bone-facing surface of the implant may be generally convex, and the external convex surface of the implant may have any of such features alone or in combination. In general, the features can be on an implant that is inserted into a bone site in a translational motion, or that is inserted into bone in a rotational motion, or that is inserted into bone in a motion that is a combination of translation and rotation such as a helical (screwing) motion.

Splines and Mesh on a Stem

Sometimes the stems of femoral implants have had longitudinal features resembling splines, suitable to engage with bone of the femur so as to resist rotation of the femoral stem around the principal axis of the femoral stem. In an embodiment of the invention, there may be provided a femoral component that has a stem that has a solid or substantially solid central region and has a region of an array of interconnected struts adjoining the solid or substantially solid central region. Furthermore, in an embodiment, the region of the array of interconnected struts could have an envelope that has a variation of shape as a function of position on a perimeter of the femoral stem. The variation could be periodic although it does not have to be. The envelope shape could have features that continue in a similar fashion at least approximately aligned with the long direction of the stem. The shape could resemble a spline. Such variation could be provided anywhere along the long direction of the stem; it could be present in some places and not in other places. This is illustrated in FIG. 17B. As a possible dimension, the envelope of the spline might have a variation that is 1 mm in dimension maximum excursion relative to what would be an enveloping surface without the extending-out feature resembling a spline. The femoral stem might be tapered, such as with a total included angle of about 3 degrees. As is illustrated in FIG. 17C, the solid region may have a shape that is not splined, although alternatively if desired the solid region could have a shape that is splined. It is not necessary that any portion of the stem have a circular cross-section. The underlying solid region could have a similar shape similar to the shape of the splines or it need not have any particular relation to the shape of the splined region.

Variation of Properties of Network of Struts

In general, a femoral stem such as for a hip replacement may have a cross-section that is elongated, especially near the end of the femur that is close to the hip ball. This means that some parts of the perimeter of the femoral stem are adjacent to bone that is more cortical (relatively more dense, relatively smaller pore size) and other parts of the perimeter are adjacent to bone that is more cancellous (relatively less dense, relatively larger pore size). In an embodiment of the invention, a stem, such as a femoral stem of a hip implant, may comprise an array of interconnected struts such that the array of interconnected struts has different properties at some portion of the perimeter compared to another portion of the perimeter.

Figure 18B:
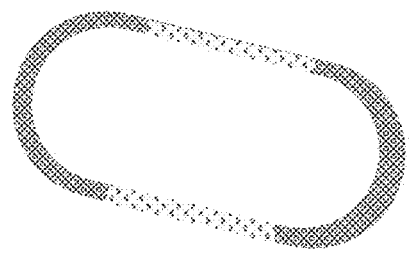
FIG. 18B is a sectional view of FIG. 18A.
Figure 18A:
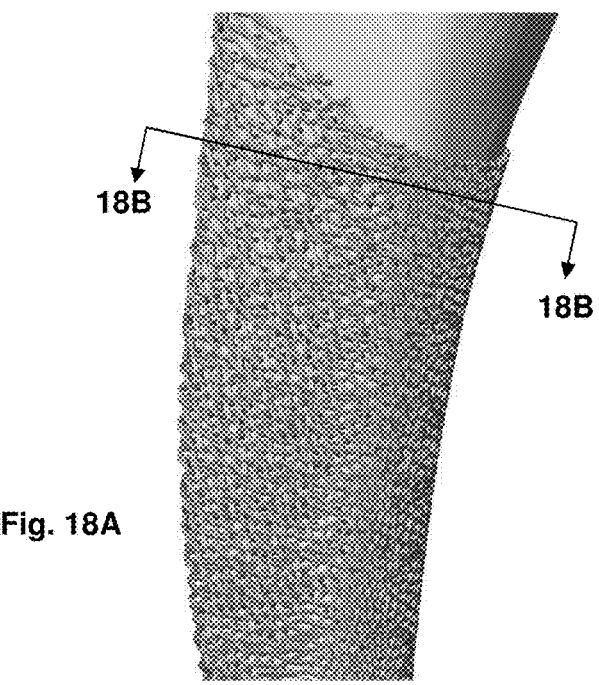
FIG. 18A shows a stem geometry having, around its perimeter, a variation of average strut length and a variation of empty volume fraction in the region that has an array of interconnected struts.

For example, referring now to FIGS. 18A-18B, at some place along such a stem, the entire perimeter or at least a portion of the perimeter may comprise interconnected struts. The stem is illustrated as being elongated in its cross-sectional shape having alonger direction in its cross-section and a shorter direction in its cross-section. At a place on the perimeter in the middle of a longer direction of the stem, the array of interconnected struts may have a relatively larger void fraction or larger average strut length or both. Conversely, at other portions on the perimeter of the stem, the array of interconnected struts may have a relatively smaller void fraction or a relatively smaller average strut length or both.

It is furthermore possible that the just-described array of interconnected struts may further have cantilevers attached to it at desired places.

Concave Implant

Embodiments of the invention such as are illustrated so far have had a bone-interfacing surface whose overall shape has been generally convex. Such implants have been intended to be implanted into a bone configuration that is generally concave. In yet another embodiment of the invention, referring now to FIG. 19, an implant can be made having features as described herein, but with an intended bone-facing surface of the implant being generally concave and suitable to adjoin or engage with a bone surface that is generally convex. In such an implant, the first region 1910, which may be solid or nearly solid similar to previously described first region 100, may be located generally on an exterior surface of the implant. The second region 1920, which may be a collection of struts similar to the previously described second region 200, may be located generally on an interior surface of the implant.

Furthermore, such a concave surface may also comprise cantilevers as described elsewhere herein in other embodiments. Such cantilevers may be connected either to an array of interconnected struts or to a solid region, or both.

Figure 19:
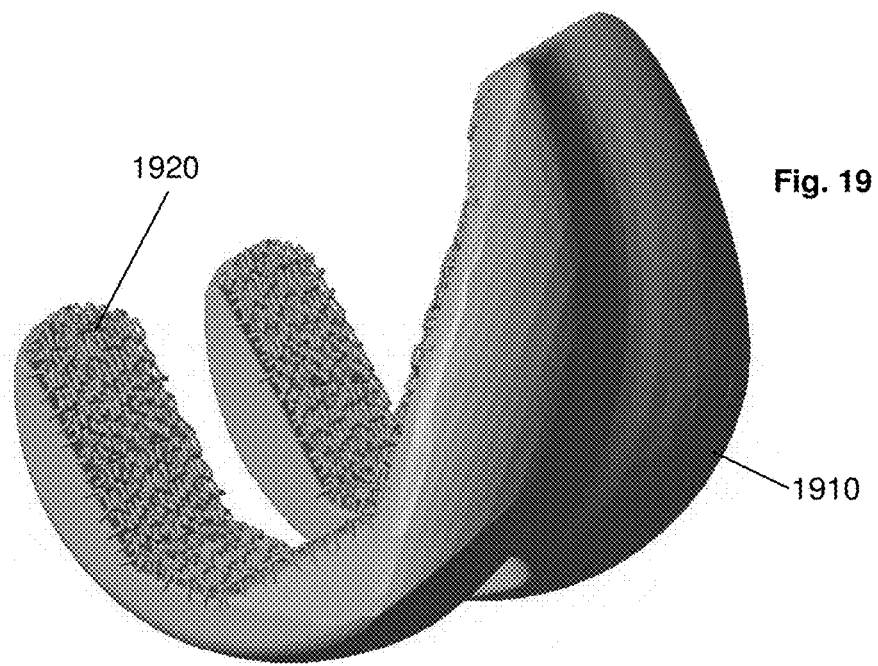
FIG. 19 shows an implant having a concave bone-facing surface, such as might be used for resurfacing a joint.

For example, an implant of this type might be an implant for resurfacing an articulating joint, as illustrated in FIG. 19. The implant that is illustrated in FIG. 19 would be suitable for resurfacing the end of the femur that articulates in the knee joint.

Instrument, Such as a Rasp

Figures 20A, 20B, 20C:
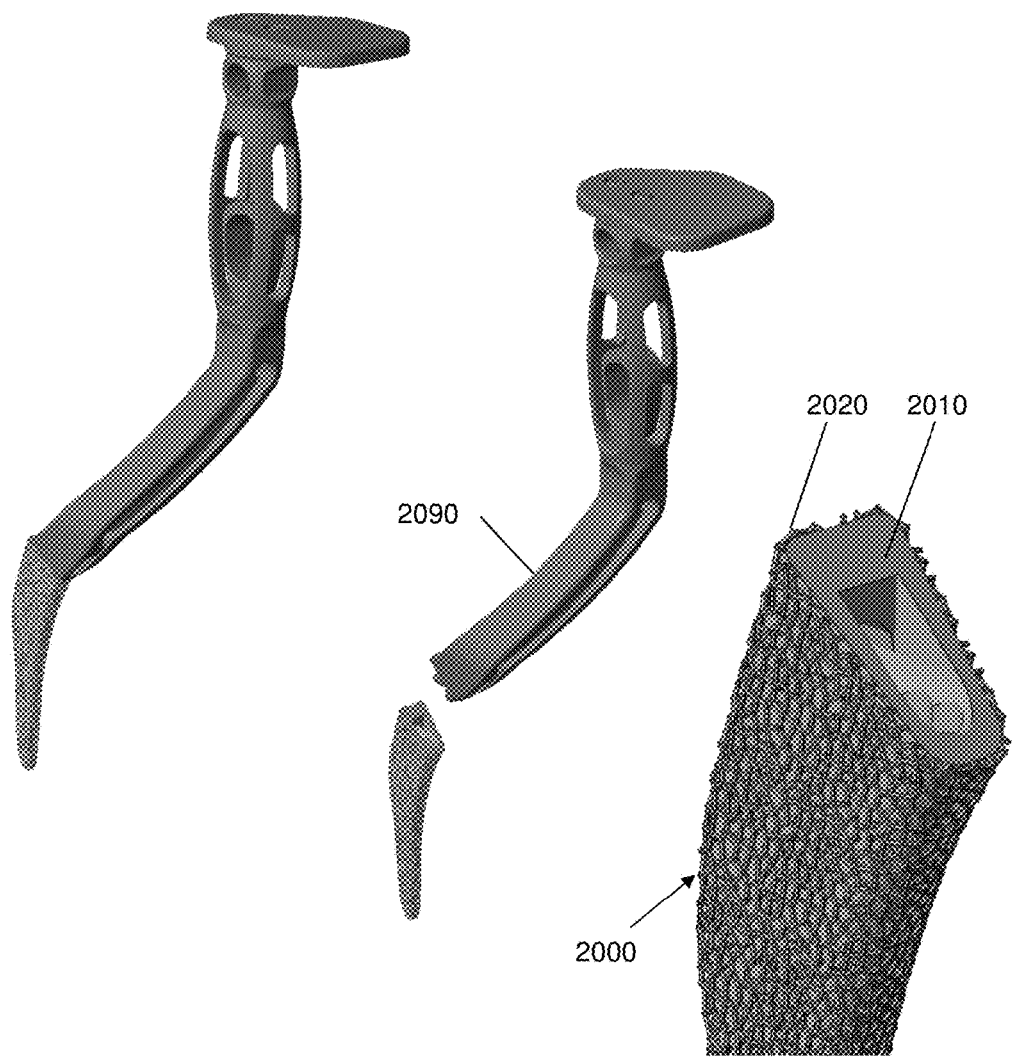
FIG. 20A shows a rasp assembled together with its handle.
FIG. 20B shows the rasp and handle of FIG. 20A, with the rasp slightly separated from its handle.
FIG. 20C is a close-up view of the rasp.
Figure 21A:
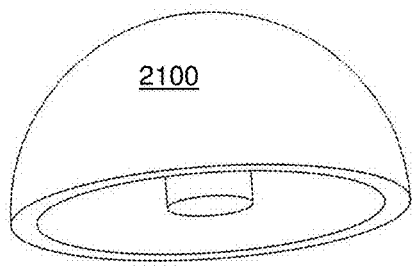
FIG. 21A is a three-dimensional perspective view showing an acetabular cup.
Figure 21B:
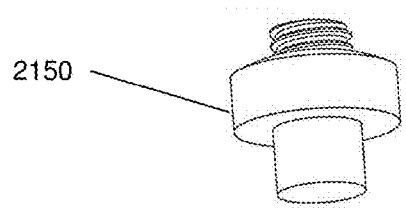
FIG. 21B is a similar view of the terminal adapter.
Figure 21C:
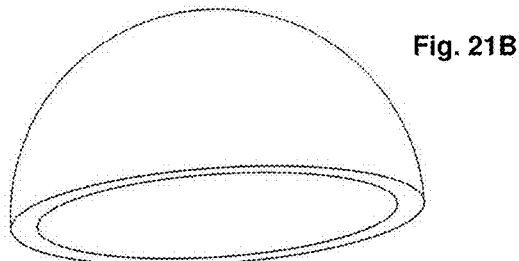
FIG. 21C is a similar view showing the terminal adapter about to be coupled to the acetabular cup.
Figure 21D:
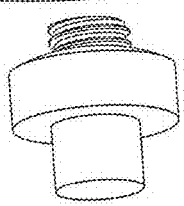
FIG. 21D shows the assembled acetabular cup and terminal being inserted into an incision in an approximately sideways orientation.
Figure 21E:
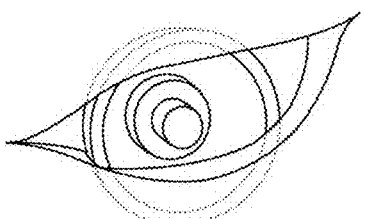
FIG. 21E shows the assembled acetabular cup and terminal already inside the surgical site and reoriented to an orientation that is approximately its final orientation.
Figure 21F:
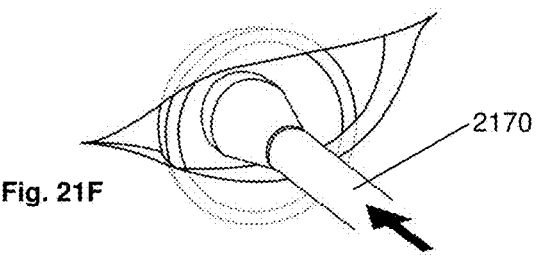
FIG. 21F shows a situation similar to that of FIG. 21E, but with an instrument coupled to the terminal adapter such as for purposes of pushing the acetabular cup into its final position.

Implants are not the only type of medical product that can be manufactured having features as described herein. In an embodiment of the invention, there may be provided an instrument having a structure such as a substantially solid region 2010 and a region 2020, adjacent to the substantially solid region, having an array of interconnected struts. Such an instrument could be a rasp such as for the purpose of preparing bone ar a surgical site. Referring now to FIGS. 20A, 20B, 20C, there is illustrated a rasp 2000 that might be used to prepare the intramedullary canal of the femur near the hip, during a hip arthroplasty procedure. Of course, other shapes of rasps or tools, comprising some of the same features, could be made used for other anatomical sites and other surgical procedures. The illustrated rasp 2000 may have an external enveloping shape that may roughly correspond to a shape of a femoral stem. It may have dimensions that are slightly smaller than respective dimensions of a corresponding femoral stem. There may be provided a handle portion 2090 and a plurality of rasp portions 2000, with the rasp portions 2000 being attachable to the handle portion 2090 and being interchangeable.

Terminal Adapter and Acetabular Cup Having a Smooth Polar Region

An acetabular cup may have a central axis of symmetry. Typically an acetabular cup has an internal feature that is suitable to engage with an instrument. For example, the internal feature may comprise an internal thread, and the instrument may have a complementary threaded feature that engages the internal thread. In such a situation, the instrument can be affixed to the acetabular cup and can be used to introduce the implant to the surgical site in a patient's body using a generally translational motion along a direction of motion. In such a situation, the central axis of symmetry of the acetabular cup may at least approximately coincide with the direction of motion for introducing the acetabular cup into the surgical site. In such a situation, the surgical incision either may be made, or at least may be able to be stretched, so that the perimeter of the incision is approximately at least the perimeter of the acetabular cup at its equator.

However, the just-described orientation for insertion is not the only possible orientation with which the acetabular cup could pass through the surgical incision. Another embodiment of the invention is an instrument for use with an acetabular cup for the purpose of providing a different orientation of introduction of the acetabular cup through the incision.

It can be realized that the profile of the acetabular cup when viewed from the side is approximately a "D" shape. In an embodiment of the invention, it would be possible to introduce the acetabular cup through the surgical incision in a sideways orientation. In such a situation, the surgical incision would have to be made, or at least would have to be able to be stretched, so that the perimeter of the incision is at least approximately the perimeter of the "D" shape of the acetabular cup. The perimeter of the "D" shape would be shorter than the perimeter of the acetabular cup at its equator. This could reduce the required size of the surgical incision.

Referring now to FIGS. 21A-21F, there is illustrated an acetabular cup 2100 and there is illustrated a terminal adapter 2150. The acetabular cup may have an interface feature such as internal thread. The terminal adapter 2150 may have a corresponding external thread that can engage the internal thread of the acetabular cup 2100. Elsewhere on the terminal adapter, the terminal adapter 2150 may have an interface feature that can engage releasably with an instrument 2170 that has a long direction. The respective orientations may be such that the central axis of symmetry of the acetabular cup may be approximately perpendicular to the long direction of the instrument.

Further in connection with such a surgical procedure, it may be realized that if acetabular cup passes through a close-fitting incision while in a sideways orientation, there is the possibility of roughness on the acetabuar cup scratching or irritating soft tissue such as at the boundary of the incision. It may further be realized that roughness at the mid-latitudes and near the equator is quite useful for bone ingrowth and for enhancing attachment to bone, but roughness near the pole of the acetabular cup is less useful for attachment. Accordingly, in an embodiment of the invention, the region near the north pole of an acetabular cup may be manufactured to be completely smooth or at least more smooth than other portions of the exterior of the acetabular cup. Such smoothness also avoids filing up spaces with skin tissue.

Also relevant to these considerations, it is even possible that during surgery an acetabular cup is brought into the surgical site and is tried and is found to be loose-fitting, and therefore it is decided to remove that cup and replace it with a different, larger cup. This possibility is an additional reason to want to minimize irritation of the soft tissue caused by passage of the acetabular cup through the incision.

The interface between the acetabular cup and the terminal adapter (if used) and the instrument may be such as to be rotationally rigid, with respect to at least one direction of rotation. This could allow the surgeon to rotate or wiggle the acetabular cup somewhat, such as for example, to scratch the bone prior to final seating of the implant.

An embodiment of the invention may comprise a surgical method in which an acetabular cup together with a terminal adapter may be inserted through a surgical incision in a generally sideways orientation with the terminal already engaged with the acetabular cup. Then, after the acetabular cup has passed through the surgical incision, the instrument may be engaged with the terminal piece. The instrument may then be used to urge the acetabular cup into position in bone.

Potential Uses of Embodiments of the Invention

Embodiments of the invention can be used with generally any joint or anatomical part that involves an implant that interfaces with bone or similar tissue.

As discussed herein, embodiments of the invention may be used for any portion of a hip replacement, such as the femoral component or the acetabular component, or for a resurfacing of any portion of the hip joint. Embodiments of the invention may be used for any portion of a knee replacement, such as the knee tibial component or the knee femoral component, or for a resurfacing of any portion of the knee. Embodiments of the invention may be used for any portion of an ankle replacement, such as the talus component or the tibial component, or for a resurfacing of any portion of the ankle.

Embodiments of the invention may be used for any portion of a shoulder replacement, such as the humeral component or the glenoid component, or for a resurfacing of any portion of the shoulder joint. Embodiments of the invention may be used for any portion of an elbow replacement, such as the humeral component or the ulnar component, or for a resurfacing of any portion of the elbow. Embodiments of the invention may be used for any portion of a wrist replacement or for a resurfacing of any portion of the wrist.

Embodiments of the invention may be used anywhere in the foot or the hand. Embodiments of the invention may be used for any hemiarthroplasty or total arthroplasty of a small joint.

Embodiments of the invention may be used as augments such as knee augments (e.g. cones, wedges), acetabular augments or other augments. Embodiments of the invention may be used as a replacement of a portion of the patella. Embodiments of the invention may be used as a wedge for an osteotomy, such as for an Evans/Cotton osteotomy or any other type of osteotomy. Embodiments of the invention may be used as an intramedullary nail. Embodiments of the invention may be used for oncologic reconstructive devices (e.g. replacement of the distal femur, or replacement of a portion of the humerus). Embodiments of the invention may be used for craniomaxillofacial applications.

Embodiments of the invention may be used in a spinal interbody device such as a cage.

Details of Mesh

Figure 2D:
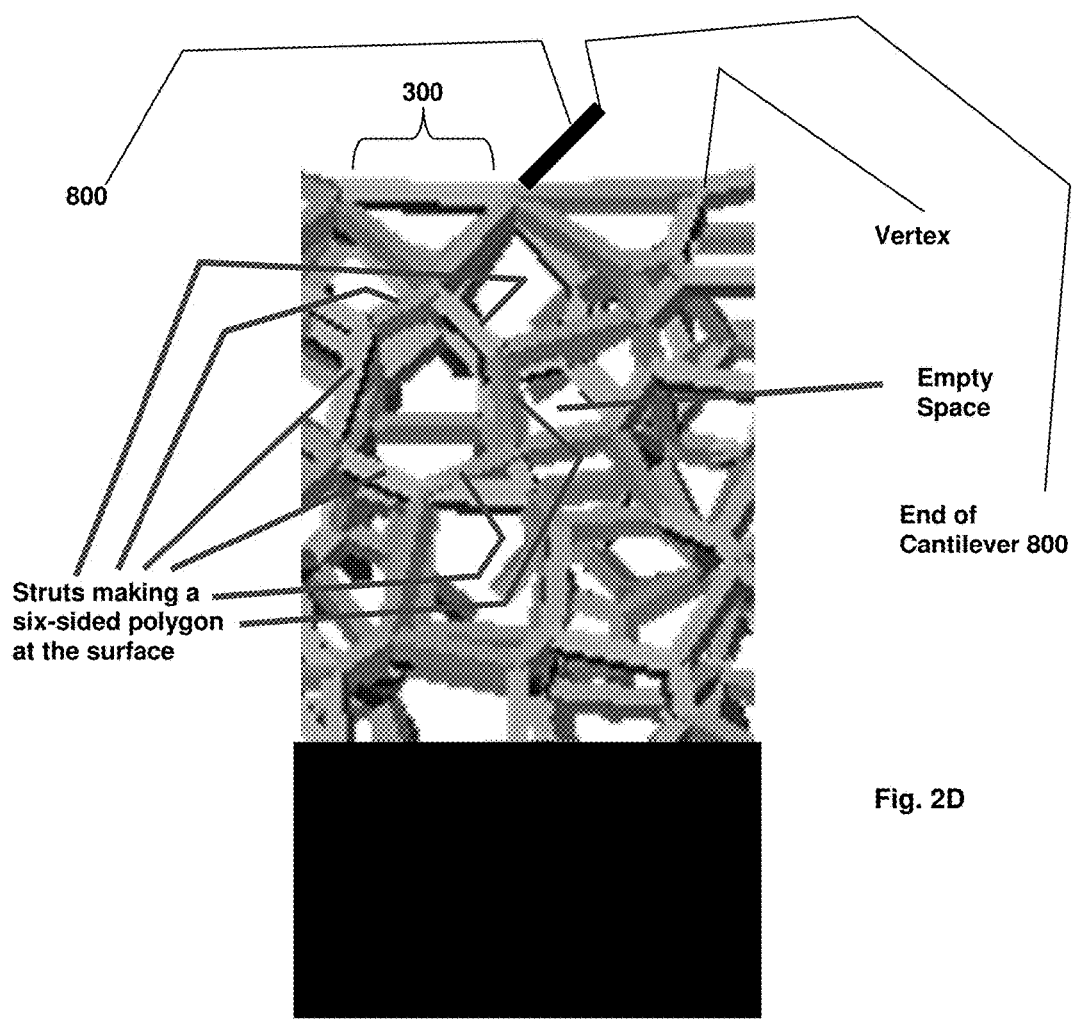
FIG. 2D is similar to FIG. 2B but is an even closer-up view of an array of struts.

Referring now to FIG. 2D, it is possible that three or more struts 300 may meet at a vertex, especially with some of the tessellation schemes as are described elsewhere herein.

A sequential series of struts 300 may form a polygon. Although the traditional mathematical definition of a polygon is a shape that occupies a plane, for present purposes, it may be considered that a polygon refers to a series of struts that forms a closed shape that either is planar or is almost planar. A polygon may be referred to as an n-gon, m-gon, o-gon, etc., with the variable n, m, o, etc. referring to the number of sides that the polygon possesses. A group of adjacent polygons may form a three-dimensional shape that is a polyhedron.

In an embodiment of the invention, the locations of the struts 300 may form a pattern that is non-repeating, i.e., does not repeat itself geometrically identically anywhere else in or on the implant 10. There may be some degree of randomness in the predetermined choice of the locations and geometry of the struts 300. The randomness may be as a result of a particular mesh generation scheme or algorithm as described elsewhere herein, although it is not wished to be limited to any particular mesh generation scheme or algorithm. Although it is not wished to be limited to this explanation, it is possible that the use of meshes that are non-repeating or even random may appropriately mimic the geometry and situation that naturally exists in living bone, with beneficial physiological and clinical results. It is to be appreciated that although the pattern of struts 300 may contain some degree of randomness and non-periodicity, that pattern is predetermined and is precisely manufactured and can be so manufactured as many times as may be desired, thereby producing multiple finished articles that are virtually identical to each other even at the level of detail of dimensions and arrangements of struts. In an implant the quantity of struts may number in the thousands or even more.

In an embodiment of the invention, the defined non-repeating nature of the array of struts 300 may manifest itself such that within a nearby region to any particular strut 300, there is no other strut that has exactly the same length as that particular strut 300. "Nearby" can be considered to be the entire implant, or it can be considered to be within a specified number, such as five, of strut-lengths away from the referenced strut.

In an embodiment of the invention, the defined non-repeating nature of the array of struts 300 may manifest itself such that within a nearby region to any particular strut, there is no other strut that is parallel to that particular strut 300.

In an embodiment of the invention, the defined non-repeating nature of the array of struts 300 may manifest itself such that within a nearby region to any particular strut 300, there is no other strut that has exactly the same spatial orientation as a particular strut 300.

A vertex included angle may be considered to be the angle made by the respective centerlines of two struts 300 at their joint at a vertex, assuming that the centerlines of the two struts 300 are each substantially straight segments. In an embodiment of the invention, the defined non-repeating nature of the array of struts 300 may manifest itself such that within a nearby region to any particular pair of struts 300 that join at a vertex, there is no other pair of struts 300 that has exactly the same included angle as that particular pair of struts 300.

In an embodiment of the invention, the defined non-repeating nature of the array of struts 300 may manifest itself such that there may be a vertex that is simultaneously a vertex of an n-gon and a vertex of an m-gon, wherein n and m are different integers. It is further possible that there may be a vertex that is simultaneously a vertex of an n-gon and a vertex of an m-gon and a vertex of an o-gon, wherein n and m and o are different integers.

In an embodiment of the invention, the defined non-repeating nature of the array of struts 300 may manifest itself such that there may be a strut 300 that is simultaneously a side of an n-gon and a side of an m-gon, wherein n and m are different integers. It is further possible that there may be a strut 300 that is simultaneously a side of an n-gon and a side of an m-gon and a side of an o-gon, wherein n and m and o are different integers.

In an embodiment of the invention, there may be surface polygons that generally lie on the external surface of the implant 10 and help define the external surface of the implant 10. In an embodiment of the invention, there may be non-surface polygons that generally do not lie entirely on the external surface of the implant 10, although they may have a side that is on the external surface of the implant 10. The overall mesh can include a mesh of surface polygons and additionally could have layers of non-surface polygons going deeper into the implant 10 before meeting the solid region 100. For example, there may be two or three or more such layers of polygons in the direction going from the surface into the interior of the mesh. However, it is to be understood that there might not be a precise definition of a layer because the various polygons may vary in their respective dimensions, numbers of sides, orientations, etc.

The mesh or array of struts could be such that the number of sides possessed by particular polygons is not identical for all polygons. For example, such a mesh may contain a polygon that is a triangle, a quadrilateral, a pentagon, a hexagon, or a polygon having an even larger numbers of sides. The number of sides could be as large as 8 or 9 or even more. It is further possible that the mesh could contain one kind of polygon, or two kinds of polygons, or three kinds of polygons, or even more than three kinds of polygons. Specifically, the mesh could comprise at least two different kinds of polygons or at least three different kinds of polygons, each kind of polygon having a different number of sides.

As an example of a mesh comprising only two different kinds of polygons, a mesh could contain at least one triangle and at least one quadrilateral. A mesh could contain at least one quadrilateral and at least one pentagon. A mesh could contain at least one pentagon and at least one hexagon.

It is further possible that there could be a mesh of greater complexity comprising three different kinds of polygons. For example, a mesh could contain at least one triangle and at least one quadrilateral and at least one pentagon. A mesh could contain at least one quadrilateral and at least one pentagon and at least one hexagon. A mesh could contain at least one pentagon and at least one hexagon and at least one heptagon. A mesh could contain at least one triangle and at least one pentagon and at least one hexagon. Other combinations of kinds of polygons are also possible.

As an example of still greater complexity, it is possible that a mesh could contain at least four different kinds of polygons.

There can be a distribution of the quantity of the polygons having various numbers of sides. For example, polygons whose number of sides is in the middle of the range of number of sides could be more common than polygons whose number of sides is at the extremes of the range of number of sides.

With regard to the surface polygons (i.e., polygons that are at the external surface of the mesh), the mesh of surface polygons may include polygons of at least two different side-numbers or at least three different side-numbers.

With regard to non-surface polygons (i.e., polygons located more interiorly), these polygons may include polygons of at least two different side-numbers or at least three different side-numbers.

With regard to all polygons, the complete set of these polygons may include polygons of at least two different side-numbers or at least three different side-numbers.

With regard to a 3-D mesh or tessellation, such a mesh may be made of polyhedra, and polyhedra may be described by the number of surfaces that make up the polyhedra. It is possible that the various polyhedra in a mesh do not all have to possess identical numbers of surfaces. The mesh may be described by the fact that the mesh can contain polyhedra of two different surface-numbers, three different surface-numbers, four different surface-numbers or even more different surface-numbers.

Method of Creating Mesh Geometry

In an embodiment of the invention, a mesh may be produced using a Voronoi mesh generation or tessellation method. Voronoi generation schemes are sometimes used for generating mathematical meshes for use in Finite Element Analysis, for analysis of experimental data, for computer graphics, and for other purposes. A Voronoi generation scheme can be used to produce a two-dimensional mesh or a three-dimensional mesh. In a two-dimensional mesh, the cells are polygons. In a three-dimensional mesh, the cells are polyhedra. A random number generator is used for a portion of the generation scheme. As a result, the mesh usually contains local lack of periodicity or lack of a repeating pattern.

Such a generation scheme starts with distributing "seeds" in a region of space using a random number generator. There may be some overall constraints imposed on the distribution of seeds. For example, the overall number of seeds generated may be constrained, as a way of constraining the average density of the resulting mesh. Another example of a constraint may be to locate the seeds more than a certain minimum distance away from each other. In instances in which the constraint is not met, seeds may be eliminated or relocated or regenerated.

After the locating of the seeds, all points may be categorized into cells according to which seed they are closest to. If the criterion is the simple criterion of distance to the nearest seed, a cell is the locus of points that are closer to a given seed than they are to any other seed. Boundaries between cells are loci of points that are equidistant from two seeds. Vertices are intersections between boundaries, and so vertices are points that are equidistant from three (or more) seeds. In a two-dimensional (planar) tessellation, cells are convex polygons. In a three-dimensional tessellation, the cells are polyhedra having a number of faces. Another possibility is that instead of a simple criterion of the boundaries being equidistant from seeds as just described, the calculation could be performed using weighting algorithms or more complicated formulas than what was just described.

Figure 22A:
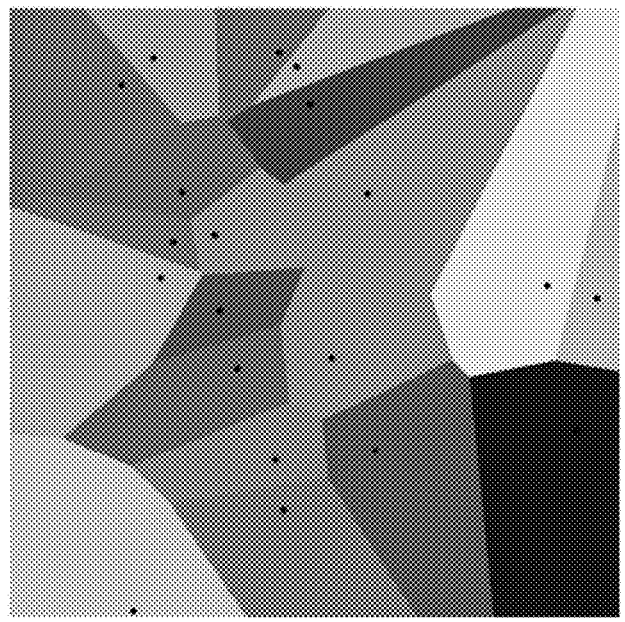
FIG. 22A is an illustration of a Voronoi tessellation in a plane.
Figure 22B:
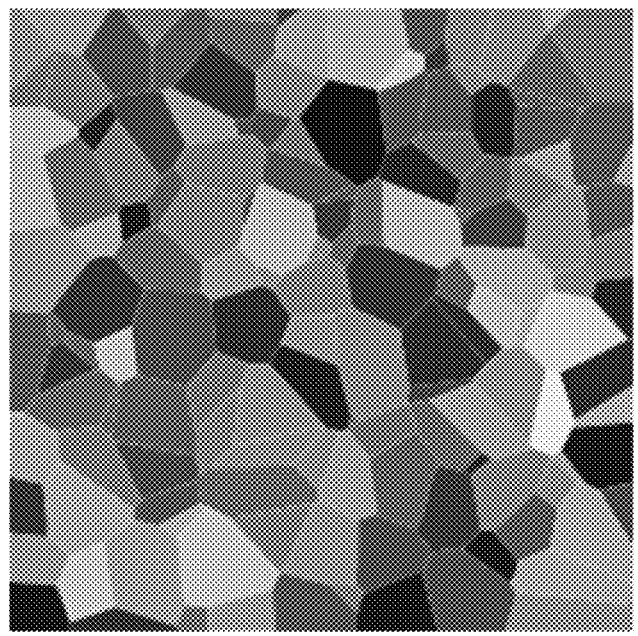
FIG. 22B is a cross-section of a three-dimensional Voronoi tessellation.

A 2-D Voronoi tessellation is illustrated in FIG. 22A. In a 2-D tessellation, the number of sides possessed by the polygons is not fixed, so a particular tesselation can contain quadrilaterals, pentagons and other kinds of polygons. In a 3-D tessellation, the numbers of faces of the polyhedra can vary, similar to the way the numbers of sides of polygons can vary in a 2-D tessellation. FIG. 22B illustrates a cross-section of a 3-D Voronoi tessellation. In general, a cross section of a 3D Voronoi tessellation is not a 2D Voronoi tessellation itself.

In an embodiment of the invention, a Voronoi generation method may be used to generate a uniquely determined geometry of interconnected struts, and that uniquely determined geometry of struts is then manufactured to form an implant 10.

A two-dimensional Voronoi tessellation can be mapped or wrapped onto a three-dimensional surface. For example, such a mesh could be mathematically stretched or modified in local places as desired. Alternatively, a three-dimensional Voronoi tessellation can be generated so as to fit within a prescribed three-dimensional shape. It is possible that the surface of the mesh can be made substantially entirely of polygons of struts, such that the polygons are planar or almost planar, and the interior of the meshed region can have struts oriented generally in all directions.

An array of struts 300 can have on its surface a mesh of polygons that at least approximately corresponds to a desired surface shape, and further can have additional struts 300 extending internally to form a three-dimensional mesh.

Method of Manufacture

The implant 10 may be manufactured according to a pre-determined, reproducible geometric pattern. Such pattern may include sufficient detail to define the location, orientation and dimensions of each individual strut 300 in the entire implant 10. Using such a method, it is possible to build any number of implants 10 that are substantially identical to each other, within manufacturing tolerances. In particular, the array of struts 300 and the mesh pattern may be substantially identical among various implants 10 built from the pre-determined description, within manufacturing tolerances.

In an embodiment of the invention, the implant 10 may be manufactured by an additive manufacturing process. Such a process may be a layer-by-layer additive manufacturing process. In such a process, a layer of powder may be deposited on a working surface. Then, energy may be deposited in appropriate places on the layer of powder appropriately to soften or melt the powder in localized places, appropriately to cause the softened or melted powder to adhere to or fuse with other powder particles or with already-solidified material in previously-deposited layers. The softening or melting may be followed by resolidification. Then, another layer of powder may be deposited and the process may be repeated. For production of a device made of metal, the powder may comprise particles of the appropriate metal. Such metal may, for example, be titanium or a titanium alloy. The energy deposition may comprise an electron beam or a laser beam, for example. Production using an electron beam may be referred to as electron beam melting. In order to deter possible undesired chemical reactions during the manufacturing process, such process may take place in a vacuum, or in an inert atmosphere. For example, the environment in which such process takes place may be controlled to have an appropriately low concentration of oxygen. The geometric locations and patterns of energy deposition may be such as to create a desired three-dimensional shape. Operation of the manufacturing process may be controlled by a computer. Equipment and services for such manufacturing are available, for example, from Arcam AB (Molndal, Sweden) and DiSanto Technology, Shelton, Conn. Other types of additive manufacturing may also be possible.

After completion of the described steps, unbound powder may be removed and any other desired post-processing may be performed. Post-processing could include conventional machining, surface treatment, chemical treatment, or any other desired steps. The product also may be rendered sterile through any appropriate sterilization method, such as gamma irradiation or ethylene oxide sterilization. The product may be packaged appropriately to maintain sterility until use.

It is not necessary to think that there is an abrupt change of local empty volume fraction at the boundary between the first region 100 and the second region 200, nor that the boundary between first region 100 and second region 200 is perfectly smooth. It is first of all possible that the boundary between first region 100 and second region 200 could be somewhat rough or irregular, such as if region 100 has a void that breaks or ends at the boundary, or if powder particles near the boundary retain some of their original shape after fusing and resolidifying. It is also not necessary that the local empty volume fraction of second region 200 near the interface with region 100 be identical to the local empty volume fraction of second region 200 a few strut-lengths away, near the bone-facing surface of second region 200. The local empty volume fraction of second region 200 could be designed to vary as might be desired along the path from the interface between first region 100 and second region 200, to the nearby bone-facing surface of second region 200.

Any of the described features can be used alone or in combination with any other features. Cantilevers could be used in combination with any other described feature. Any of the described features can be used to enhance mechanical fixation of the implant relative to bone, either at the time of implantation or at some time after surgery after either partial or full healing and bone ingrowth. Any of the described features can be optimized for local empty volume fraction, local average strut length, interconnectivity between openings, and external surface roughness within a specified boundary. Any of the described features can be formed to generate macroscopic structures as features of the boundary surface to provide for mechanical fixation. Any of the described features may serve to prevent rotation, subsidence, or expulsion, and further may serve as a mechanical fixation and porous mesh for biologic fixation by bone ingrowth or ongrowth.

As discussed herein, it is possible to use described features or apparatus with generally any shape of implant for generally any part of the body. It is possible to use more than one of the techniques or features or apparatus described herein, in any combination. All referenced documents are incorporated by reference herein in their entirety. Although embodiments have been disclosed herein, it is desired that the scope be limited only by the attached claims.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of"

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. An implantable device, comprising:
a first region that is substantially solid; and
a second region, adjacent to said first region, said second region comprising a plurality of interconnected struts, some of said struts joining said first region, said struts having an average strut length, said struts defining openings between said struts through which bone can grow,
wherein said second region comprises struts that are connected at both of their ends to other struts and are outermost struts and define an exterior having a bone-facing enveloping surface,
wherein said bone-facing enveloping surface has at least one concavity and at least one convexity,
wherein said bone-facing enveloping surface has a majority external enveloping surface occupying a majority of an exterior of said second region,
wherein said bone-facing enveloping surface further comprises a macroscopic surface-interrupting feature that differs from said majority external enveloping surface,
wherein said macroscopic surface-interrupting feature comprises some of said interconnected struts, and
wherein said majority external enveloping surface of said implantable device is at least approximately a hemisphere having a pole and an equator, and said convexity has a convexity height relative to said majority external enveloping surface, and said convexity height is greater at a location near said equator than it is at a location closer to said pole.

2. The implantable device of claim 1, wherein said at least one concavity comprises at least one of a curved concave region and a valley and a concave corner, and wherein said at least one convexity comprises at least one of a curved convex region and a convex corner and a convex peak.

3. The implantable device of claim 1, wherein said at least one convexity is selected from the group consisting of an engagement ridge, a crest, a fin, a fin having a tooth, and a divertor structure.

4. The implantable device of claim 1, wherein said implantable device comprises a plurality of said convexities, and said plurality of said convexities are distributed in a regular pattern on said implantable device.

5. The implantable device of claim 1, wherein said at least one convexity has a leading end with respect to a direction of advancement of said implantable device, and said leading end is sharp, and wherein said at least one convexity has a trailing end with respect to said direction of advancement of said implantable device, and said trailing end is blunt.

6. The implantable device of claim 1, wherein said bone-facing enveloping surface is interrupted in at least one place by a feature comprising solid material that is continuous with said first region.

7. The implantable device of claim 1, wherein where said first region has an overall density that is at least 90% of a solid density of a material from which said first region is made.

8. The implantable device of claim 1, wherein said implantable device further includes a longitudinal axis and, in a cross-section taken perpendicular to said longitudinal axis, has a perimeter, wherein at some places said perimeter is farther from said longitudinal axis than said perimeter is at other places, by at least one of said average strut length.

9. The implantable device of claim 1, wherein an overall shape of said bone-facing enveloping surface is selected from the group consisting of generally convex and generally concave.

10. The implantable device of claim 1, wherein said implantable device is selected from the group consisting of: a femoral component of a hip replacement; an acetabular component of a hip replacement; a resurfacing of any portion of a hip joint; a tibial component of a knee replacement; a femoral component of a knee replacement; a resurfacing of any portion of a knee joint; a talar component of an ankle replacement; a tibial component of an ankle replacement, or for a resurfacing of any portion of an ankle joint; a glenoid component of a shoulder replacement; a humeral component of a shoulder replacement; a resurfacing of any portion of a shoulder joint; a humeral component of an elbow replacement; an ulnar component of an elbow replacement; a resurfacing of any portion of an elbow joint; any portion of a wrist replacement; a resurfacing of any portion of a wrist joint; a replacement or resurfacing of any joint in a foot or a hand; a hemiarthroplasty or total arthroplasty of a small joint; a knee augment; an acetabular augment; another augment; a replacement of a portion of a patella; a wedge for an osteotomy; an intramedullary nail; oncologic reconstructive devices; for craniomaxillofacial applications; a spinal cage; and any portion of a fixed or movable spinal interbody device.

11. The implantable device of claim 1, wherein said macroscopic surface-interrupting feature has a thickness of at least one of said average strut length.

* * * * *